US011291671B2

(12) United States Patent
Slattery et al.

(10) Patent No.: US 11,291,671 B2
(45) Date of Patent: Apr. 5, 2022

(54) SOLID DRUG IMPLANTS FOR INTRACOCHLEAR DELIVERY OF THERAPEUTICS FOR THE TREATMENT OF OTIC DISORDERS

(71) Applicant: O-Ray Pharma, Inc., Pasadena, CA (US)

(72) Inventors: William H. Slattery, La Cañada Flintridge, CA (US); Thomas Smith, Santa Monica, CA (US); Erik Pierstorff, Sierra Madre, CA (US); Marc M. Baum, Pasadena, CA (US)

(73) Assignee: O-Ray Pharma, Inc., Pasadena, CA (US)

( * ) Notice: Subject to any disclaimer, the term of this patent is extended or adjusted under 35 U.S.C. 154(b) by 0 days.

(21) Appl. No.: 15/154,530

(22) Filed: May 13, 2016

(65) Prior Publication Data

US 2016/0250231 A1 Sep. 1, 2016

Related U.S. Application Data

(62) Division of application No. 14/380,193, filed as application No. PCT/US2013/028036 on Feb. 27, 2013, now abandoned.

(60) Provisional application No. 61/603,602, filed on Feb. 27, 2012.

(51) Int. Cl.
| | |
|---|---|
| *A61K 31/573* | (2006.01) |
| *A61K 9/00* | (2006.01) |
| *A61K 9/50* | (2006.01) |
| *A61K 31/56* | (2006.01) |

(52) U.S. Cl.
CPC .......... *A61K 31/573* (2013.01); *A61K 9/0046* (2013.01); *A61K 9/0092* (2013.01); *A61K 9/5026* (2013.01); *A61K 9/5073* (2013.01); *A61K 31/56* (2013.01)

(58) Field of Classification Search
CPC .. A61K 9/0046; A61K 9/0092; A61K 9/5073; A61K 31/573
See application file for complete search history.

(56) References Cited

U.S. PATENT DOCUMENTS

| | | | |
|---|---|---|---|
| 4,410,323 A | 10/1983 | Hodosh et al. | |
| 5,607,697 A | 3/1997 | Alkire et al. | |
| 5,885,783 A | 3/1999 | Yoo et al. | |
| 6,368,658 B1 | 4/2002 | Schwarz et al. | |
| 6,440,102 B1* | 8/2002 | Arenberg | A61F 11/00 604/506 |
| 9,688,676 B2 | 6/2017 | Owens | |
| 10,118,901 B2 | 11/2018 | Chen et al. | |
| 2003/0039689 A1 | 2/2003 | Chen et al. | |
| 2003/0229333 A1 | 12/2003 | Ashton et al. | |
| 2004/0038406 A1 | 2/2004 | Unger et al. | |
| 2004/0172005 A1 | 9/2004 | Arenberg et al. | |
| 2006/0013858 A1 | 1/2006 | Trune | |
| 2006/0025391 A1 | 2/2006 | Lulla et al. | |
| 2007/0160648 A1 | 7/2007 | Ashton et al. | |
| 2009/0062896 A1* | 3/2009 | Overstreet | A61K 9/0046 607/137 |
| 2009/0292237 A1 | 11/2009 | Overstreet et al. | |
| 2009/0306225 A1 | 12/2009 | Lichter et al. | |
| 2010/0036000 A1* | 2/2010 | Lighter | A61K 47/10 514/772.1 |
| 2011/0071493 A1 | 3/2011 | Lobl et al. | |
| 2015/0044271 A1 | 2/2015 | Slattery et al. | |

FOREIGN PATENT DOCUMENTS

| | | |
|---|---|---|
| CN | 1589166 A | 3/2005 |
| CN | 104159635 A | 11/2014 |
| EP | 2819741 A1 | 1/2015 |
| GB | 2459910 A | 11/2009 |
| WO | 2000050593 A1 | 8/2000 |
| WO | 2004058223 A1 | 7/2004 |
| WO | 2009045464 A1 | 4/2009 |
| WO | 2010091733 A1 | 8/2010 |
| WO | 2013130619 A1 | 9/2013 |

OTHER PUBLICATIONS

Goldenberg, David, et al., Am J Otolaryngol (2002); 23: pp. 142-147 (Year: 2002).*
Halpin, Chris, et al., Steroid Therapy for Sudden Sensorineural Hearing Loss, (Dec. 4, 2003) pp. 1-6 (Year: 2003).*
Paksoy et al (Medical Oncology, online Mar. 19, 2010, vol. 28, pp. 615-621) (Year: 2010).*
PCT/US2013/028036 International Search Report and Written Opinion dated Apr. 30, 2013; 10 pages.
PCT/US2013/028036 International Preliminary Report on Patentability dated Sep. 2, 2014; 8 pages.
EP Application No. 13754828.5 Extended European Search Report dated Jun. 19, 2015; 5 pages.
Chinese Application No. 201380011205.3 Examination Report dated Dec. 25, 2015; 10 pages.
Lecaroz et al. Poly(D,L-Lactide-Coglycolide) Particles Contaiing Gentamicin: Pharmacokinetics and Pharmacodynamics in Brucella melitensis-Infected Mice. Antimicrobial Agents and Chemotherapy (2007). 51 (4):1185-1190.
Wolgemuth. A Look at Parylene Coatings in Drug-Eluting Technologies. Medical Device & Diagnostic Industry Magazine (Aug. 1, 2005); pp. 1-3.

* cited by examiner

*Primary Examiner* — Mark V Stevens
(74) *Attorney, Agent, or Firm* — Nixon Peabody LLP; Linda B. Huber

(57) ABSTRACT

The present invention provides for pharmaceutical preparations, devices, systems and methods for the treatment of otic diseases and conditions. In various embodiments, the preparations, devices, systems and methods enable sustained drug release for the treatment or prevention of hearing loss, infections, and other pathological conditions of cochlea and inner ear.

32 Claims, 7 Drawing Sheets

SOLID DRUG IMPLANTS FOR INTRACOCHLEAR DELIVERY OF THERAPEUTICS FOR THE TREATMENT OF OTIC DISORDERS

CROSS-REFERENCE TO RELATED APPLICATIONS

This application claims the benefit of priority under 35 U.S.C. § 121 as a divisional of U.S. application Ser. No. 14/380,193, filed Aug. 21, 2014, which is a National Phase of International Application No. PCT/US2013/028036, filed Feb. 27, 2013, which designated the U.S. and that International Application was published under PCT Article 21(2) in English, which also includes a claim of priority under 35 U.S.C. § 119(e) to U.S. provisional patent application No. 61/603,602, filed Feb. 27, 2012, the entirety of which is hereby incorporated by reference.

FIELD OF THE INVENTION

This invention relates to the fields of pharmaceuticals, drug delivery devices, methods for sustained drug release, and methods for treatment of hearing loss, infections, and other pathological conditions of cochlea and inner ear.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

1. Sensorineural Hearing Loss

Sensorineural hearing loss (SNHL) is a major medical problem with over 32 million Americans affected by hearing loss. The most common form of hearing loss is presbycusis or aging hearing loss while other causes of hearing loss include noise exposure (acoustic or physical trauma), genetic predisposition, viral and bacterial infections, ototoxic medications, Meniere's disease, autoimmune disease and idiopathic causes.

2. Chemically-Induced Hearing Loss.

Hearing loss afflicts over ten percent of the population of the United States. Causes of hearing loss include loud noise, aging, infections, and ototoxic chemicals. Damage to the peripheral auditory system is responsible for a majority of such hearing deficits. In particular, destruction of hair cells and primary afferent neurons in the spiral ganglia, which transduce auditory signals from the hair cells to the brain, has been implicated as major causes of hearing loss.

The peripheral auditory system comprises auditory receptors, hair cells in the organ of Corti, and primary auditory neurons, the spiral ganglion neurons in the cochlea. Spiral ganglion neurons ("SGN") are primary afferent auditory neurons that deliver signals from the peripheral auditory receptors, the hair cells in the organ of Corti, to the brain through the cochlear nerve. The eighth nerve connects the primary auditory neurons in the spiral ganglia to the brain stem. The eighth nerve also connects vestibular ganglion neurons ("VGN"), which are primary afferent sensory neurons responsible for balance and which deliver signals from the utricle, saccule and ampullae of the inner ear to the brain.

The vestibular and auditory systems share many characteristics including peripheral neuronal innervations of hair cells and central projections to the brainstem nuclei. Both of these systems are sensitive to ototoxins that include therapeutic drugs, antineoplastic agents, contaminants in foods or medicines, and environmental and industrial pollutants. Ototoxic drugs include non-steroidal anti-inflammatory drugs such as acetylsalicylic acid and diclofenac, the widely used chemotherapeutic agent cisplatin and its analogs, commonly used aminoglycoside antibiotics, e.g. gentamicin, certain macrolide antibiotics (L. She, et al., 1999, Am. J. Health-Syst. Pharm. 56:380-383), glycopeptide antibiotics such as vancomycin, quinine and its analogs, salicylate and its analogs, and loop diuretics.

Salicylates, such as aspirin, have long been used for their anti-inflammatory, analgesic, anti-pyretic and anti-thrombotic effects. Unfortunately, salicylates have ototoxic side effects. They often lead to tinnitus ("ringing in the ears") and temporary hearing loss, and if used at high doses for a prolonged time, hearing impairment can become persistent and irreversible (J. A. Brien, 1993, Drug Safety 9:143-148).

The toxic effects of these drugs on auditory cells and spiral ganglion neurons are often the limiting factor in their therapeutic usefulness. For example, the aminoglycoside antibiotics (gentamicins, streptomycins, kanamycins, tobramycins, and the like) are broad-spectrum antimicrobials effective against gram-positive, gram-negative and acid-fast bacteria. They are used primarily to treat infections caused by gram-negative bacteria, often in combination with beta lactams which provide synergistic effects. Advantages to using the aminoglycoside antibiotics include a low incidence of *Clostridium difficile* diarrhea relative to other antibiotics, and a low risk of allergic reactions. However, the aminoglycosides are known to exhibit serious ototoxicity, especially at higher (and more effective) doses. For example, 25% of patients given one gram of streptomycin daily for 60 to 120 days displayed some vestibular impairment, whereas at two grams per day, the incidence increased to 75%, and some patients suffer permanent damage (see U.S. Pat. No. 5,059,591). For this reason the aminoglycosides are rarely selected by physicians as a first-line therapy, despite their many advantages.

The most effective and frequently used loop diuretics (such as ethacrynic acid, furosemide, and bumetanide) are known to cause ototoxicity. Several less-commonly used loop diuretics also have been experimentally shown to cause ototoxicity; this group includes torsemide, azosemide, ozolinone, indacrinone, and piretanide. Hearing loss associated with loop diuretics is frequently, but not always, reversible.

Ototoxicity is a serious dose-limiting side-effect for cisplatin (cis-diammine-dichloroplatinum(II), CDDP), a widely-used antineoplastic agent that has proven effective on a variety of human cancers including testicular, ovarian, bladder, and head and neck cancers. The toxic side effects of cisplatin (peripheral neuropathies, myelo-suppression, gastrointestinal toxicity, nephrotoxicity, and ototoxicity) are well-known. The routine administration of mannitol, hypertonic saline, and high fluid administration have largely ameliorated cisplatin-induced nephrotoxicity, leaving ototoxicity as the primary dose-limiting factor today.

For equivalent inner ear concentrations, cisplatin is the most ototoxic drug known. Generally, cisplatin ototoxicity is irreversible, its onset insidious, and the hearing loss may progress after discontinuation of the protocol. Hearing loss is usually permanent, although partial recovery may occur in some cases. Thus, although an increasing number of cancer patients are surviving modern regimens of chemotherapy, they frequently suffer from cisplatin-induced hearing loss.

Cisplatin damages both the auditory and vestibular systems. The primary ototoxic effects of cisplatin appear to occur in the cochlea. Anatomical changes occur in both the stria vascularis and the organ of Corti. The primary histologic findings include dose-related hair cell degeneration and damage to the supporting cells, and at high doses, total collapse of the membranous labyrinth can occur. In the organ of Corti, there is loss of outer and inner hair cells, with a propensity for outer hair cell loss in the basal turn, and alterations in the supporting cells and Reissner's membrane. Softening of the cuticular plate and an increased number of lysosomal bodies in the apical portion of the outer hair cell has also been reported.

The molecular mechanisms underlying these changes are largely unknown. Several potential mechanisms have been described, including impaired deoxyribonucleic acid (DNA), ribonucleic acid (RNA), and protein synthesis; impaired synthesis and degradation of prostaglandins, gangliosides, mucopolysaccharides, and lipids; and disruptions in metabolism and ion transport.

Accordingly, there exists a need for means to prevent, reduce or treat the incidence and/or severity of inner ear disorders and hearing impairments involving inner ear tissue, particularly inner ear hair cells, and optionally, the associated auditory nerves. Of particular interest are those conditions arising as an unwanted side-effect of ototoxic therapeutic drugs including cisplatin and its analogs, aminoglycoside antibiotics, salicylate and its analogs, or loop diuretics. In addition, there exists a need for methods which will allow higher and thus more effective dosing with these ototoxicity-inducing pharmaceutical drugs, while concomitantly preventing or reducing ototoxic effects. Thus, a medical need exists for a method that provides a safe, effective, and prolonged means for prophylactic or curative treatment of hearing impairments related to inner ear tissue damage, loss, or degeneration, particularly ototoxin-induced and particularly involving inner ear hair cells.

3. Noise-Induced Hearing Loss.

Noise-induced hearing loss (NIHL) describes hearing loss after exposure to intense noise levels, wherein the damage is to the inner ear, specifically, the cochlea. This type of hearing loss is generally caused by chronic exposure to high intensity continuous noise with superimposed episodic impact or impulse noise. Both an intense sound presented to the ear for a short period of time and a less intense sound that is presented for a longer time period can produce equal damage to the inner ear. The majority of chronic NIHL is due to occupational or industrial exposure. However, a non-occupational form of NIHL, called socioacusis, may result from gunfire, loud music (via concerts or headphones), open vehicles such as motorcycles, snowmobiles or tractors, and power tools to name just a few. Although the hearing damage is often symmetrical, i.e., both ears are affected, there are cases, such as hearing loss due to frequent target shooting, which result in asymmetric hearing loss.

Upon exposure to impulse noise, such as an explosive blast, a patient may suffer significant tympanic membrane and middle ear damage. In chronic exposure, which generally occurs at lower intensity levels, middle ear and tympanic membrane damage are unlikely. In noise exposure, the primary and initial damage is generally cochlear, with secondary neural degeneration of the auditory system occurring over time. Noise-induced hearing loss has been reviewed by K. Campbell in "Essential Audiology for Physicians" (1998), San Diego: Singular Publishing Group, Inc.

4. Inflammation

Inflammation in the inner ear is a common symptom of a variety of maladies of the ear, including physical, ototoxic and noise induced trauma, autoimmune inner ear disease and infection. Inner ear inflammation has various debilitating indicators, including ear pain, dizziness, vertigo, and tinnitus. Acute and chronic inflammation can lead to hair cell and spiral ganglion neuron death and can permanently impair hearing. The most common treatment for inner ear inflammation is the administration of corticosteroids, whether administered systemically or locally via injection.

5. Autoimmune Inner Ear Disease

Immune-mediated cochleovestibular disorders (IM-CVDs) represent a syndrome of SNHL, often associated with vertigo, tinnitus, and aural fullness, believed to be caused by an autoimmune mechanism. The sequelae of IMCVDs include devastating disabilities: profound deafness and serious vestibular dysfunction. Autoimmune inner ear disease (AIED) is a treatable cause of SNHL.

Autoimmune inner ear disease (AIED) is a rare form of idiopathic progressive, often bilateral, SNHL that occurs over weeks to months. Vestibular symptoms such as vertigo, generalized imbalance, and ataxia are often present. Additionally, these patients often respond to high-dose corticosteroids, suggesting that inner ear inflammation may be important in this syndrome.

The prevalence of AIED is unknown. The National Institute of Deafness and Other Communicative Disorders (NIDCD) estimates that approximately 615,000 individuals in the United States are currently diagnosed with Meniere's disease and that 45,000 new cases are diagnosed each year. However, a study of 575 patients with Meniere's Disease revealed that 63 (11%) were also diagnosed with autoimmune disease.

The first report of recognized treatable autoimmune ear disease is credited to McCabe in 1979. A patient was treated with surgery for chronic ear disease and associated sensorineural hearing loss. The wound had not healed until a pathology report revealing vasculitis prompted the initiation of systemic steroids. The wound then healed and the sensorineural hearing loss improved. McCabe speculated that there was an autoimmune process in the inner ear that resolved after immunosuppression with chronic cortisone and cyclophosphamide therapy. In the ensuing years, the diagnosis of AIED was confirmed by a positive response to immunosuppressive therapy.

Since the McCabe report, multiple reports of progressive hearing loss associated with systemic autoimmune diseases have been published. Cogan's syndrome, Bechet's disease, relapsing polychondritis, systemic lupus erythematosus, rheumatoid arthritis, polyarteritis nodosum, and inflammatory bowel disease have all been linked with sensorineural hearing loss and dizziness. Disease control or management with immunosuppressive drugs has been effective in reversing or stabilizing hearing loss in some patients. Crohn's disease, ulcerative colitis, Wegener's granulomatosis, fibromyalgia syndrome (FMS), and chronic fatigue syndrome (CFS) are systemic diseases of autoimmune etiology that have been reported to have associated sensorineural hearing loss. In one of the larger studies, Heller et al. [1998] reviewed the clinical presentation and sera of 132 patients with sudden hearing loss or progressive hearing loss and found phospholipid antibodies in nearly 50% of both groups. Additionally, serotonin and ganglioside antibodies were detected in 53% of the patients with sudden hearing loss and 63% of the patients with progressive hearing loss. Twenty-eight of the 132 patients revealed symptoms typical for FMS or CFS including fatigue, myalgia, arthralgia, depression, sicca syndrome, and diarrhea. Because of the association of antibodies known to be present with these diseases and hearing loss, Roland [2000] recommended questioning patients that present with hearing loss for symptoms of FMS and CFS.

Also, a growing body of evidence has emerged including the documentation of antibodies to a 68-kD inner ear antigen and the benefit from immunosuppressive therapy supporting the possibility of an immune-mediated mechanism in these disorders.

Tissue necrosis factor-alpha (TNF-α) has been shown to play a critical role in several chronic inflammatory conditions. It has been shown to be present in the inner ear structures and may also play a critical role in the pathogenesis of IMCVD. The spiral ligament fibrocytes from the murine cochlea produce high levels of TNF-α when stimulated by inflammatory cytokines. Intratympanic injection of TNF-α causes expression of inducible nitric oxide synthase (iNOS/NOS II) in the cochlea of guinea pigs, which may have neurotoxic effects on the inner ear. TNF-α enhances the proliferation of utricle supporting cells in the avian inner ear, which is a significant event during sensory regeneration after injury. TNF-α diminishes the survival of statoacoustic neurons from the avian inner ear. Scherer et al. [2010] reported that TNF-α constricted the spiral modiolar artery, the functional end artery feeding the inner ear, in a gerbil model via activation of sphingosine-1-phosphate signaling. This observed reduction of cochlear blood flow may be a possible mechanism for TNF-α-induced SNHL.

6. Meniere's Disease

Meniere's disease is a disorder of the inner ear characterized by episodes of severe dizziness (vertigo), ringing in the ear (tinnitus), hearing loss, and a feeling of fullness in the ear. Meniere's disease usually affects only one ear. The vertigo attacks come on suddenly and without warning. Severe Meniere's disease patients suffer from multiple disabling dizzy spells. Some patients will have attacks of dizziness separated by long periods of time. Others may experience many attacks close together over a number of days. The National Institute of Deafness and Other Communicative Disorders (NIDCD) estimates that approximately 615,000 individuals in the United States are currently diagnosed with Meniere's disease and that 45,000 new cases are diagnosed each year.

Currently, there is no FDA-approved drug product for treatment or prevention of Meniere's disease. Treatment has been focused on relieving symptoms. Dietary salt restriction and diuretics are the mainstay of therapy. Anticholinergics, antiemetics, and sedatives may provide temporary relief during an acute spell. The most disabling symptom, severe vertigo, is somewhat controlled by medical therapy in approximately 80% of patients while approximately 20% of patients require a more aggressive treatment plan due to recurrent disabling vertigo spells. Historically, surgery was recommended for individuals with severe vertigo uncontrolled with medical therapy. Intratympanic injections of dexamethasone have been reported successful in some patients with Meniere's disease. While this therapy may be beneficial for some patients there is a subset of patients that will require more aggressive treatment.

Intratympanic injection of gentamicin is a common procedure and growing in popularity. Although introduced by Schuknecht in 1956, only recently in the United States has widespread interest developed in using aminoglycosides intratympanically to treat unilateral Meniere's disease. Intratympanic gentamicin is sometimes referred to as a chemical labyrinthectomy whereby a surgeon injects an aminoglycoside formulation through the intact tympanic membrane into the middle ear with a spinal needle and the gentamicin is allowed to absorb into the cochlea through the round window. The pitfalls of intratympanic gentamicin include inconsistent efficacy and hearing loss. Both of these problems may be attributable to inconsistent and variable dosing regimens.

7. Otitis Media.

Otitis media is an inflammation of the middle ear, most commonly associated with viral or bacterial infection. A relatively high percentage of the population, particularly children, are affected. In children, the disease is most often associated with upper respiratory afflictions which trigger a transudate secretion response in the Eustachian tube and middle ear. Bacteria and viruses migrate from the nasopharynx to the normally air-filled middle ear via the Eustachian tube, and can cause the Eustachian tube to become blocked, preventing ventilation and drainage of the middle ear. Fluid then accumulates behind the eardrum, causing pain and inflammation.

Otitis media is the most common cause of hearing loss among children. Although otitis media is readily treated with antibiotics and is ordinarily not serious, frequent and/or untreated otitis media may permanently damage a child's hearing. Fluid remaining in the middle ear can cause repeated bouts of acute otitis media, and if the condition becomes chronic it may result in frequent recurrences of acute infections. In the more severe forms of otitis media, purulent exudate, toxins and endogenous anti-microbial enzymes accumulate in the middle ear, which can cause irreparable damage to sensory-neural and sound conducting structures. Damage to the eardrum, the bones of the ear, or the auditory nerves caused by such infections can cause permanent hearing loss. Hearing loss may also result from impairment, damage or destruction of inner ear cochlear hair cells, as damaging substances in the middle ear space gain access to the inner ear via diffusion through the round window membrane.

8. Treatment and Prevention of Otic Disorders.

One hypothesis to account for hearing impairment due to loud noise, age or chemicals points to reactive oxygen species (ROS) as being the causative agents for cochlear hair cell damage. Some free radical scavengers, iron chelators and certain NMDA receptor antagonists have been shown to be otoprotective agents, which are effective in protecting cochlear hair cells from chemically-induced or noise-induced cell death. Accordingly, approaches to treat hearing impairment due to idiopathic sudden sensory hearing loss (ISSHL), noise induced hearing loss (NIHL), or chemically induced hearing loss (CIHL) have included treatment with otoprotective agents, including antioxidants such as aspirin, reduced glutathione, N-methyl-(D)-glucaminedithiocarbamate, (D)-methionine, and iron chelators such as tartrate and maleate. While these compounds have shown efficacy in some animal models of NIHL and CIHL, to date, only D-methionine has been approved for use to prevent or treat hearing impairment. However, the pharmacological profile of (D)-methionine makes it difficult to administer it to patients.

Other treatments for ototoxicity have involved administration of steroids, vitamins or rheologic agents. Other treatments include the use of vasodilators; vascular rheologic agents such as pentoxyfylline; anticoagulants; plasma expanders such as dextran; renograffin or urograffin, and growth factors such as IGF-1 and FGF-2.

Another difficulty in preventing ototoxicity, especially when due to aminoglycoside antibiotics, is that the damage occurs over a period of time that extends well beyond the time during which the ototoxic agent is administered. Aminoglycosides, for example, can be detected in the cochlea months after the last dose of the drug. Any chemotherapy intended to ameliorate ototoxicity must therefore be administered over a considerable period of time.

There is a pressing need for otoprotective agents that prevent, reduce, or otherwise treat hearing impairment due to noise, age or chemicals. These otoprotective agents would be useful in the context of hazards posed by loud noises in certain occupational or recreational activities, injuries arising from exposure to ototoxic chemicals such as those that occur in certain chemotherapeutic regimes, or improving quality of life in aging populations experiencing progressive hearing impairment. For instance, the ototoxicity of aminoglycosides has limited the applications of this very important group of antibiotics, and the ototoxicity of cisplatin adds a further burden to those already facing a life-threatening disease. There is a particular need for otoprotective agents that prevent, reduce, or otherwise ameliorate the ototoxic side-effects of aminoglycoside antibiotics or platinum-containing antineoplastic agents, without compromising the in vivo microcidal or anti-tumor properties of these compounds. Where ototoxicity is the dose-limiting side effect of a chemotherapeutic agent, there is also a need for otoprotective agents that would lift the dose limitation, making it possible to administer higher and more effective doses of the chemotherapeutic agent.

Local administration of neurotoxins, such as botulinum toxin, to middle ear muscles has been disclosed as a method of treating tinnitus, cochlear nerve dysfunctions, and Meniere's disease (U.S. Pat. No. 6,265,379). Other treatments include systemic administration of benzodiazepines and topical anesthetics such as lidocaine. Systemic administration of such drugs is associated with severe side-effects, however, and the therapeutic effect is short-lived without repeated administration of the drugs. There is a need for a method of administration of benzodiazepines and local anesthetics to the middle and inner ear that avoids systemic exposure while providing extended therapeutic benefits.

Treatments for ISSHL include administration of vasodilators, such as papaverine, histamine, nicotinic acid, procaine, and niacin; rheologic agents such as pentoxyfylline, heparin and warfarin; anti-inflammatory agents, particularly corticosteroids; antiviral agents such as acyclovir, famciclovir, valacyclovir and amantadine; and diatrizoate meglumine. Here as well, there is a need for a method of providing therapeutic levels of these drugs within the ear, for a prolonged period of time, without exposing the subject's entire system to the drugs and their potential side-effects.

For individuals at high risk for middle ear infections, antibiotics may be systemically administered in a prophylactic manner. Systemic administration of antibiotics to combat or prevent middle ear infection generally involves a prolonged lag time to achieve therapeutic levels within the ear, requires high initial doses in order to achieve such levels, and in some cases may require administration over a very long period of time. Systemic administration of a drug is affected by pharmacokinetic variables such as rates of absorption, rates of metabolism, and rates of excretion that vary from patient to patient. These drawbacks complicate the ability to obtain and maintain therapeutic levels, and systemic toxicities may preclude the prophylactic use of some antibiotics altogether. There is a need, therefore, for a method of providing therapeutically effective concentrations of antibiotics in the middle and inner ear over a prolonged period of time, without the disadvantages of systemic administration.

SUMMARY OF THE INVENTION

The invention relates to the treatment of otic disorders by local and sustained administration of appropriate therapeutic agents to the cochlea. More specifically, the present invention relates in one embodiment to the use of otoprotective agents in the cochlea to prevent, reduce, or otherwise treat hearing impairments, particularly those due to ISSHL, CIHL, NIHL, aging, inflammation, disease, or infection.

The present invention relates to the use of otoprotective agents to prevent, reduce, or otherwise treat ototoxicity associated with NIHL, aging, inflammation, disease, or CIHL. In the case of CIHL due to chemotherapeutic agents, the invention relates to the use of otoprotective agents in a manner that does not compromise the efficacy of chemotherapeutic agents.

Accordingly, one aspect of the present invention describes a method for preventing, reducing or otherwise treating NIHL, CIHL, or hearing impairment due to aging inflammation, or disease by administering to a patient a pharmaceutical dosage of an otoprotective agent, or a pharmaceutically acceptable salt, solvate, clathrate, prodrug, tautomer or a metabolic derivative thereof.

Still further, the present invention provides a method for treating the ototoxic effects currently associated with certain antibiotics, and particularly with the more popular and commonly used aminoglycoside and macrolide antibiotics without sacrificing antimicrobial effectiveness.

Still further, the invention provides a method for treating the ototoxic effects currently associated with certain chemotherapeutics, and particularly with the more popular and commonly used cisplatin chemotherapeutics without sacrificing the antineoplastic effectiveness of cisplatin or its analogs.

Still further, the present invention provides a method for treating the ototoxic effects currently associated with certain quinines and quinidines without sacrificing their effectiveness. The adverse side effects of quinine and quinidine are similar, and have been given the name "cinchonism," deriving from the fact that quinine is obtained from the bark of the cinchona tree. These side effects include disturbances of hearing, including tinnitus, deafness, and vertigo.

Another object of the invention is the method of treatment of patients, particularly children, having purulent otitis or other chronic ear infections, comprising the use of a sustained release drug device described herein to obtain an effective local concentration of antibiotic in the ear. Another object of the invention is the provision of effective local concentrations of an analgesic to the affected ear of a patient suffering from otitis.

Accordingly, in one aspect, the present invention provides a method for preventing or reducing ototoxicity in a patient undergoing treatment with an aminoglycoside antibiotic, comprising administering to the patient a locally effective amount of an otoprotective agent.

In another aspect, the present invention provides a method for preventing or reducing ototoxicity in a patient undergoing treatment with a loop diuretic agent.

In yet a further aspect, the present invention provides a method for preventing or reducing ototoxicity in a patient undergoing treatment with quinine or quinidine for conditions in which such compounds are indicated.

In another aspect, the present invention provides a method for preventing or reducing ototoxicity in a patient exposed to noise for a time and at an intensity sufficient to result in ototoxicity.

The invention provides sustained-release devices, adapted for insertion into the cochlea, for administration of otoprotective agents, as well as a method of reducing the ototoxic effect of a chemotherapeutic agent upon a subject which comprises inserting into an inner ear cavity of the subject a sustained-release device of the invention. In particular embodiments, the inner ear cavity is the cochlea.

Furthermore, an improvement in the present invention relates to methods for augmenting treatments which require administration of a chemotherapeutic agent that has an ototoxic and hearing-impairing side effect. The improvement includes administering prophylactically or therapeutically an effective amount of an otoprotective agent to prevent, reduce or treat the ototoxic side effects of the chemotherapeutic drug without impairing its efficacy. The otoprotective agent and chemotherapeutic agent may be provided in various modes including administration prior to, simultaneously with, or subsequent to administration of said ototoxic chemotherapeutic agent. The otoprotective agent and chemotherapeutic agent may also be provided in various forms including but not limited to a single pharmaceutical preparation, e.g., as a single dosage form, or a kit in which each is provided in separate dosages, along with instructions for co-administering the two agents.

Another aspect of the invention provides a method for treating a mammal to prevent, reduce, or treat a hearing impairment, disorder or imbalance, including but not limited to ototoxin-induced hearing impairment, by administering to a mammal in need of such treatment an otoprotective agent formulated in a sustained release device. One embodiment is a method for treating a hearing disorder or impairment wherein the ototoxicity results from administration of a therapeutically effective amount of an ototoxic pharmaceutical drug. Typical ototoxic drugs include but are not limited to chemotherapeutic agents, e.g. antineoplastic agents, and antibiotics. Other ototoxic drugs include loop diuretics, quinines or a quinine-like compound, and salicylate or salicylate-like compounds.

In various embodiments, the ototoxic compound is an antibiotic, particularly, an aminoglycoside, macrolide, or glycopeptide antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2. Ototoxic macrolide antibiotics include but are not limited to erythromycin and azithromycin. Glycopeptide antibiotics include but are not limited to vancomycin. In these embodiments, the methods of the present invention are effective to reduce the ototoxic effects.

Hearing impairments induced by aminoglycosides can be prevented or reduced by the methods of the invention. Although the aminoglycosides are particularly useful due to their rapid bactericidal action in infections by susceptible organisms, their use is limited to more severe, complicated infections because of ototoxic and nephrotoxic side-effects. For this reason the aminoglycosides are considered to have a low therapeutic/risk ratio compared to other antibiotics used systemically.

The aminoglycoside antibiotics which can be employed in conjunction with the ototoxicity inhibiting compositions of the invention may be any aminoglycoside antibiotic. Examples of such aminoglycoside antibiotics include but are not limited to kanamycin, gentamicin, amikacin), dibekacin, tobramycin, streptomycin, paromomycin, sisomicin, isepamicin, and netilmicin, all known in the art. Other useful antibiotics include the many structural variants of the above compounds (e.g. kanamycins A, B and C; gentamicins A, C1, C1, C2 and D; neomycins B and C, and the like).

Accordingly, the methods and compositions of the invention find use for the prevention and treatment of opportunistic infections in animals, including humans.

Compositions and methods of the invention may be used advantageously in combination with known antimicrobial agents to provide improved methods for prevention and treatment diseases induced by Gram-positive, Gram-negative, and acid-fast bacteria. Use of a composition of the invention in combination with such agents permits a higher dosage of the antimicrobial agents, increasing therapeutic (e.g., antibacterial) effectiveness without increasing the risk of ototoxic side effects.

Various embodiments of the present invention provide for a method, comprising: providing a pharmaceutical preparation for sustained-release of an active pharmaceutical ingredient (API) after cochlear administration or implantation, comprising: one or more core particles adapted for administration or implantation into the cochlea, wherein each core particle comprises the API, wherein the pharmaceutical preparation is not in a liquid suspension; and administering or implanting into the cochlea the pharmaceutical preparation to provide sustained-release administration of the API. In various embodiments, the one or more core particles are each coated with a first polymeric coating formed from a first polymer-forming solution to form the one or more coated core particles.

Various embodiments provide for a sustained-release drug delivery system for delivering a medicament to the cochlea, comprising: 1 to 15 devices adapted for administration or implantation into the cochlea, each device comprising: a solid drug core particle comprising the medicament, the solid drug core particle having a maximum dimension between 20 μm and 800 μm and a maximum length of 4 mm, wherein the device is capable of releasing said medicament at a rate which maintains a pharmacologically effective concentration of said medicament within the cochlea, wherein the 1 to 15 devices are not in a liquid suspension.

Various embodiments provide for a pharmaceutical preparation for sustained-release of an active pharmaceutical ingredient (API) after cochlear administration or implantation, comprising: 1 to 15 core particles adapted for administration or implantation into the cochlea, wherein each core particle comprises the API, wherein the pharmaceutical preparation is not in a liquid suspension.

BRIEF DESCRIPTION OF THE FIGURES

The following drawings are illustrative of embodiments of the invention and are not meant to limit the scope as encompassed by the claims.

DETAILED DESCRIPTION OF THE INVENTION

Figure 1:
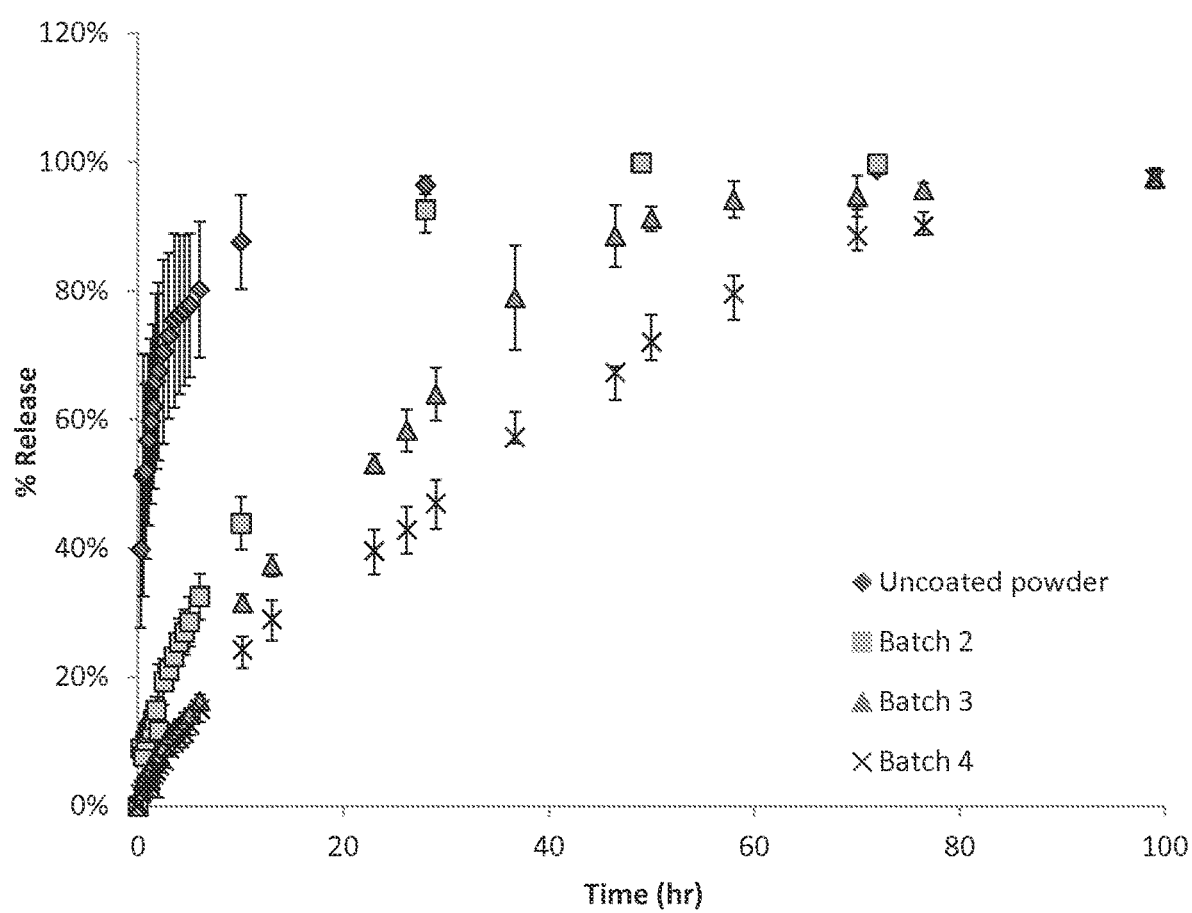
FIG. 1 depicts data regarding in vitro release of an active pharmaceutical ingredient (fluticasone proprionate) from coated particles of the invention over a sustained-release period in 70% methanol, 30% water in accordance with various embodiments of the present invention.
Figure 2:
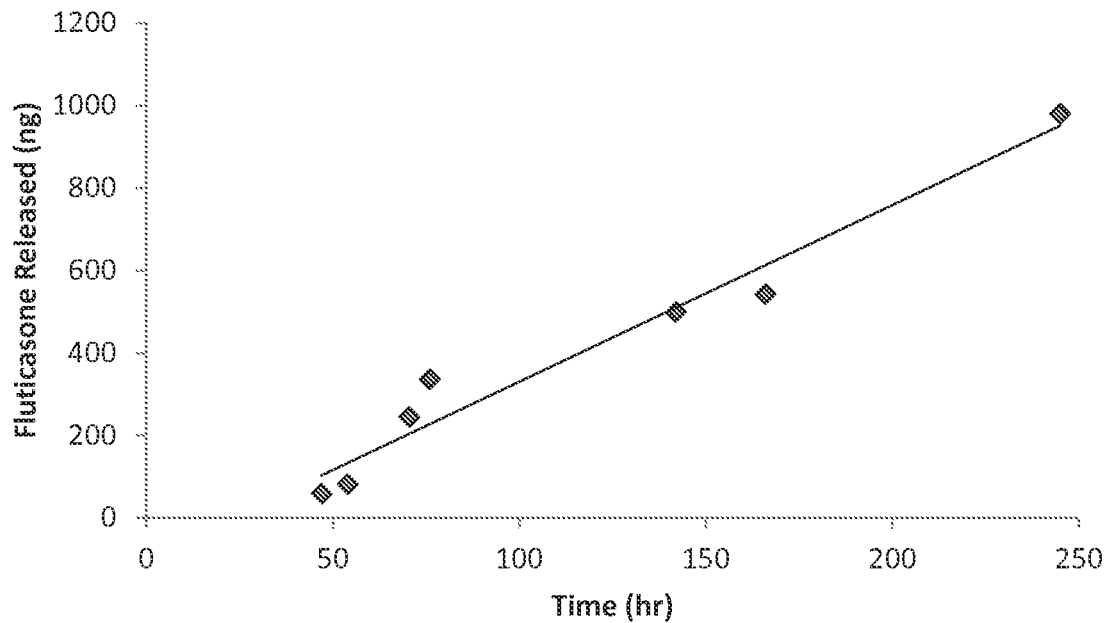
FIG. 2 depicts data regarding the in vitro release of an active pharmaceutical ingredient (fluticasone proprionate) from coated particles of the invention over a sustained-release period in an environment analogous to cochlear perilymph in accordance with various embodiments of the present invention.

All references cited herein are incorporated by reference in their entirety as though fully set forth. Unless defined otherwise, technical and scientific terms used herein have the same meaning as commonly understood by one of ordinary skill in the art to which this invention belongs.

By "adapted for insertion into the cochlea" is meant that the composition or device is of a size suitable for insertion into the cochlea via a syringe, cannula, catheter, or similar device, and that surfaces which are exposed to body fluids and tissues are biocompatible. An appropriate size for a device is between 20 and 800 µm in diameter. The composition or device may be bioerodible, or it may resist bioerosion, in which case the composition or device may be designed for later removal, or it may be designed to remain in place indefinitely. A device according to the invention may be single-use, or optionally it may be designed to be re-filled at intervals with a therapeutic agent. It should be understood that all references to insertion of a device or composition are intended to apply to insertion of multiple individual devices or compositions. Instruments and methods suitable for inserting devices and medicaments into the inner ear are known in the art, as disclosed, for example in U.S. Pat. Nos. 4,819,647, 5,476,446, 6,377,849, and 6,408,855.

The terms "sustained-release device" and "device" refer to any object which comprises a drug, pro-drug, or co-drug, and which is capable of releasing said drug, pro-drug, or co-drug at a steady rate over a prolonged period of time ranging from four days to a year or more, when implanted into a body. It includes erodible compositions, which may optionally be coated or encapsulated, and it also may include non-erodible reservoir devices, which may be single-use or refillable. The compositions and devices of the present invention are suitable for insertion into the cochlea include dry drug particles and encapsulating devices, which can be viewed as containers for a medicament, wherein the medicament slowly diffuses through one or more openings or pores in the surface of the capsule. Also included are devices in which a medicament-containing core is surrounded entirely or in part by a permeable coating, through which the medicament gradually diffuses. Such devices may be manufactured for example by filling a pre-formed device, or by coating a pre-formed medicament core.

Active pharmaceutical ingredient ("API") and "medicament" are used interchangeably herein.

The term "hearing loss" refers to both a complete loss of hearing due to noise, chemicals, infection, inflammation, disease, or age, or to a hearing impairment due to the aforementioned factors. The term "hearing impairment" refers to a diminished hearing capacity due to the aforementioned factors.

As used herein, the term "ototoxic" or "ototoxicity" includes, but is not limited to, any detrimental or pathologic change in the structure or function of the ear, including changes in hearing and balance. Auditory functional changes can include, but are not limited to, hearing loss or other changes in auditory threshold for any stimulus, perception of sound including recruitment (abnormal growth in the perception of loudness), ability to identify, localize, recognize, distinguish between, or process sounds, and/or distortion of sounds or any abnormality as identified by conventional auditory tests. This term also includes tinnitus (ringing or noises in the ear), which includes any perception of sound other than in response to an external signal. Further, ototoxicity includes any perceived or measured functional change in the balance or vestibular system, including, but not limited to, either induced or spontaneous vertigo, dysequilibrium, increased susceptibility to motion sickness, nausea, vomiting, nystagmus, syncope, lightheadedness, dizziness, difficulty in visual tracking secondary to vestibular or balance disorder or abnormality as measured on any test of vestibular or balance function. Structural changes can include any intra- or extra-cellular, multicellular, or organ change in the auditory or vestibular pathways from the external ear up through and including the cortex and all pathways in between.

By "ototoxic agent" in the context of the present invention is meant a substance that through its chemical action injures, impairs, or inhibits the activity of a component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin, taxol, or dideoxy-compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillin or chloramphenicol, or megadoses of vitamins A, D, or B6, salicylates quinines and loop diuretics. Other toxic agents that can cause ototoxicity-inducing hearing impairment can be identified and characterized by methods as taught herein. Radiation is also an ototoxic agent for purposes of this disclosure.

By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

The term "otoprotective agent" refers to an agent that reduces, prevents, treats NIHL, CIHL or age induced hearing impairment, or prevents, ameliorates, or otherwise protects against ototoxicity or hearing impairment.

The term "otodestructive" means that which causes hearing impairment.

The term "ototoxic chemotherapeutic drug" refers to a chemotherapeutic agent with an ototoxic, hearing-impairing side effect.

As used herein, "mammal" for purposes of treatment refers to any animal classified as a mammal, including humans, domestic, and farm animals, and zoo, sports, or pet animals, such as dogs, horses, cats, sheep, pigs, cows, etc. For the purposes of the present invention the preferred mammal is a human.

"Treatment" refers to both therapeutic treatment and prophylactic or preventative measures, wherein the object is to prevent or slow down (lessen) inner ear tissue-damage-related hearing disorder or impairment (or balance impairment). Those in need of treatment include those already experiencing a hearing impairment, those prone to having the impairment, and those in which the impairments are to be prevented (reduce the risk of occurrence). The hearing impairments are due to inner ear hair cell damage or loss, wherein the damage or loss is caused by infections, mechanical injury, loud sounds, aging, inflammation, disease, or chemical-induced ototoxicity.

As used herein "chronic" refers to a disorder that is not acute but rather occurs more or less on a continuous level. A "disorder" is any condition that would benefit from treatment with the method, and compositions of the invention. The disorder being treated may be a combination of two or more of the above disorders, and may include auditory or vestibular neuron damage or loss.

As used herein, the term "preventing" means to reduce the risk of occurrence of an abnormal biological or a medical event, such as hearing loss, in a cell, a tissue, a system, animal or human.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and relieving one or more symptoms the disease, disorder or condition, i.e., causing regression of the disease, disorder and/or condition.

The term "clathrate" refers to inclusion compounds in which the guest molecule is in a cage formed by the host molecule or by a lattice of host molecules.

The term "prodrug" refers to any compound that is converted to a more pharmacologically active compound under physiological conditions (i.e., in vivo). A common method for making a prodrug is to select moieties that are hydrolyzed under physiological conditions to provide the desired biologically active drug.

The term "metabolic derivative" refers to a compound derived by one or more in vitro or in vivo enzymatic transformations on the parent compound, wherein the resulting derivative has an $ED_{50}$ value as a therapeutic agent that is less than 1000 times the $ED_{50}$ value of the parent compound.

The term "aminoglycoside antibiotic" includes a broad class of amino sugar containing antibiotics well known in the art. The aminoglycoside agents described in the literature which are useful in the methods of the present invention include, but are not limited to, amikacin (BB-K8), butirosin, geneticin, gentamicin, kanamycin, lividomycin, neomycin, paromomycin, hybrimycin, propikacin (UK 31214), ribostamycin, seldomycin, trehalosamine, α-D-mannosyl-α-D-glucosaminide, apramycin, bluensomycin, netromycin, streptomycin, sisomicin, destomycin, antibiotic A-396-I, dibekacin, kasugamycin, fortimicin, netilmicin, hygromycin, and tobramycin, and derivatives, analogs or variants thereof. Also useful in the methods of the invention are ototoxic glycopeptide antibiotics such as vancomycin, and ototoxic macrolide antibiotics such as erythromycin.

The term "platinum-containing antineoplastic agents" includes a broad class of water-soluble, platinum coordination compounds well known in the art, typically having anti-tumor activity. The platinum-containing antineoplastic agents described in the literature which are useful in the methods of the present invention include, but are not limited to, cis-diaminedichloro-platinum(II) (cisplatin), trans-diaminedichloro-platinum(II), cis-diamine-diaquaplatinum (II)-ion, cis-diaminedichloroplatinum(II)-ion, chloro(diethylenetriamine)-platinum(II) chloride, dichloro (ethylenediamine)-platinum(II), diamine(1,1-cyclobutanedicarboxylato)-platinum(II) (carboplatin), spiroplatin, dichlorotrans-dihydroxybisisopropolamine platinum IV (iproplatin), diamine(2-ethylmalonato)platinum (II), ethylenediamine-malonatoplatinum(II), aqua(1,2-diaminodiclohexane)-sulfatoplatinum(II), (1,2-diaminocyclohexane)malonato-platinum(II), (4-carboxyphthalato)(1,2-diaminocyclo-hexane)-platinum(II), (1,2-diaminocyclohexane)-(isocitrato)platinum(II), (1,2-diaminocyclohexane)-cis(pyruvato)platinum(II), and (1,2-diaminocyclohexane)-oxalatoplatinum(II).

Diseases of the ear are categorized into diseases of external, middle and inner ear. One symptom common to all of these conditions is hearing loss. Hearing loss is characterized as conductive or sensorineuronal loss. Conductive loss is a rare condition, except for *glomus* jugulare tumors and neuromas of the seventh nerve with extension into the middle ear. Sensorineuronal loss can be further subdivided into neuronal or retrocochlear and sensory or cochlear losses. Causes of neuronal or retrocochlear hearing loss include acoustic neuroma or cerebellopontine angle lesions. With rare exceptions, neurotologic diseases cause a sensorineuronal type of hearing loss. The characteristics of a cochlear loss, however, reflect hair cell damage with an intact eighth nerve. Common causes of cochlear hearing loss include sudden hearing loss, ototoxicity, noise-induced hearing loss, congenital and early onset hearing loss, presbycusis, and metabolic causes. Particular hearing impairments relevant to the invention are sensory hearing loss due to end-organ lesions involving inner ear hair cells, e.g., acoustic trauma, viral endolymphatic labyrinthitis, Meniere's disease, inflammation, physical trauma. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness, including those of viral origin, e.g., viral endolymphatic labyrinthitis caused by viruses including mumps, measles, influenza, chickenpox, mononucleosis and adenoviruses. The hearing loss can be congenital, such as those caused by rubella, anoxia during birth, bleeding into the inner ear due to trauma during delivery, ototoxic drugs administered to the mother, erythroblastosis fetalis, and hereditary conditions including, Waardenburg's syndrome and Hurler's syndrome. The hearing loss can be noise-induced, generally due to a noise greater than 85 decibels (db) that damages the inner ear. Hearing loss includes presbycusis, which is a sensorineural hearing loss occurring as a normal part of aging, fractures of the temporal bone extending into the middle ear and rupturing the tympanic membrane and possibly the ossicular chain, fractures affecting the cochlea, and acoustic neurinoma, which are tumors generally of Schwann cell origin that arise from either the auditory or vestibular divisions of the 8th nerve. In particular, the hearing loss may be caused by an ototoxic drug that affects the auditory portion of the inner ear, particularly inner ear hair cells. More detailed information about the etiology of hearing loss can be found, for example, in Chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments. These chapters are incorporated by reference herein as though fully set forth.

Another group of disorders are noise-induced hearing loss and presbycusis (hearing loss due to aging). Some of the recognized factors involved in these types of hearing loss are genetic, vascular, noise, dietary, hypertension, and metabolic causes. These occur due to a gradual, usually symmetrical loss of sensory hair loss and nerve fibers. The degeneration is initially sensory and the neural degeneration is presumably secondary. Typical pharmaceutical compounds that may be useful to treat these conditions include, but are not limited to, calcium channel blocking agents, immunosuppressants, such as cyclosporins, neuromodulators, steroids, and growth factors, such as IGF-1, FGF-2 and BDNF.

Another group of disorders which may cause sensorineuronal hearing loss, and which are treatable by the methods, compositions, and devices of the invention, are the peripheral vestibular disorders. The peripheral vestibular system consists of the vestibular portion of cranial nerve (CN) VIII and the balance organs of the inner ear: the utricle, the saccule, and the semicircular canals. Lesions of these organs affect the balance function and cause vertigo and disequilibrium. Some of the disorders may be associated with various degrees and combinations of hearing loss, tinnitus, hyperacusis, or diplacusis. Peripheral vestibular disorders are subdivided into primary and secondary causes or lesions. Primary lesions begin in and are limited to the inner ear or vestibular nerve. Secondary lesions begin elsewhere, such as in the middle ear or cranial base, and progress to involve the inner ear.

Endolymphatic hydrops is a peripheral vestibular disorder with a primary lesion of the inner ear that has many different causes. Endolymphatic hydrops is characterized by distention and distortion of the endolymph-containing structures of the labyrinth. Hydrops usually manifests as episodic vertigo, fluctuating sensory hearing loss, tinnitus, and aural fullness. Some known causes of endolymphatic hydrops are acoustic trauma, autoimmune inner ear disease, chronic otitis media, Cogan's syndrome, congenital deafness fenestration of the otic capsule, labyrinthine concussion, Letterer-Siwe disease, leukemia, Lindau-von Hippel disease, Mondini dysplasia, otosclerosis, Paget's disease, serous labyrinthitis, surgical inner ear trauma, syphilis, temporal bone trauma, and viral labyrinthitis. When a specific cause cannot be identified, the condition is termed Meniere's disease.

Meniere's disease (idiopathic endolymphatic hydrops) is characterized by an episodic abnormal sensation of movement when there is no motion or an exaggerated sense of motion in response to a given bodily movement (vertigo), progressive loss of hearing in one or both ears, and abnormal noises or ringing in the ear (tinnitus). The fluid-filled semicircular canals ("labyrinth") of the inner ear, along with the eighth cranial nerve, control balance and position sense. Meniere's disease involves a swelling of the part of the canal (endolymphatic sac) that controls the filtration and excretion of the fluid of the semicircular canal. Some risk factors for developing Meniere's disease include recent viral illness, respiratory infection, stress, fatigue, use of prescription or nonprescription drugs including aspirin, and a history of allergies, smoking, and alcohol use.

While prompt treatment of an ear infection and other related disorders may help prevent Meniere's disease, there remains a need for a more targeted therapy. As there is no known cure for Meniere's disease, treatment has focused on relieving symptoms by lowering the pressure within the endolymphatic sac. Long term therapy for hydrops aims to decrease inner ear fluid volume by dietary sodium restriction and diuresis. Diuresis is achieved by combination therapy with antidiuretics such as thiazide, triamterene, or carbonic anhydrase. Associated side effects include hypokalemia. Vasodilators have also been used in treating Meniere's disease. Betahistine, niacin, and papaverine are some vasodilators that have been employed with limited success. Therefore, treatment for Meniere's disease is generally directed at reducing inner ear fluid volume, increasing inner ear blood circulation, and/or arresting the effect of immune reactivity or hydropic damage that has occurred.

Vestibular suppressant medications are another group of drugs that have been used in controlling vertigo in peripheral vestibular disorders. These drugs have variable anticholinergic, anitemetic, and sedative properties. Diazepam, meclizine, dimenhydrinate, prochlorperazine, promethazine, and preazepam are some examples of this group of drugs. In some rare cases when the patient's vertigo is uncontrollable, hospitalization may be necessary. In such cases, intravenous or intramuscular fentanyl citrate and droperidol are very effective. However, these drugs are potent respiratory depressants and their systemic administration must be closely monitored.

In addition to vestibular suppressants several anticholinergic medications may occasionally be useful in managing Meniere's patients. Glycopyrrolate, propantheline, and atropine can be effective in mitigating nausea and atypical or minor forms of vertigo. Scopolamine is useful in ameliorating motion sickness.

Corticosteroids have also been used to limit the inflammatory response. Steroids such as dexamethasone or prednisone can often reverse sudden hearing loss that sometimes occurs in hydrops patients that have been symptom-free for months or years. Steroids are co-administered with antacids and histamine H2 blockers to counter their side effects.

Another mode of treating Meniere's disease is unilateral chemical vestibular ablation via the instillation into the tympanic cavity of ototoxic drugs such as aminoglycosides. Severe hearing loss is usually the side effect of this treatment.

Use of many of these medications is limited due to severe side effects associated with systemic administration. Systemic administration of cyclophosphamide, for example, for treatment of autoimmune autologic dysfunction leads to manifestation of neutropenia.

Additionally, this drug is contraindicated in treating patients with a history of bleeding ulcers or poorly controlled insulin-dependent diabetes. Diuretics, which are the mainstay of treating conditions associated with hydrops, may cause hyperkalemia which is associated with muscle cramps, weakness, lassitude, and some cardiac arrhythmias.

Surgical treatment of Meniere's disease relieves vertigo symptoms by totally ablating the erratically reacting labyrinth, but entails complete loss of hearing in the affected ear. Conservative surgical approaches which attempt to conserve auditory functions while treat vertigo symptoms include endolymphatic sac decompensation, cochleostomy, cochlear dialysis, sacculotomy, grommet insertion, cervical sympathectomy, vestibular nerve division, ultrasonic destruction of the vestibular labyrinth, and interatympanic injection of ototoxic drugs. Radical surgical approach involves the total destruction of the membranous labyrinth. A surgical approach is often contraindicated because of the high incidence of complete hearing loss in the ear caused by surgically opening the inner ear. Therefore, there still exists a need for treating conditions such as Meniere's disease and other disorders associated with cochlear hair cell loss, where more effective methods are employed other than dietary precautions, systemic drug administration, or surgically opening the inner ear.

Medicines which are typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), and other drugs, biological materials, and pharmaceutical compositions suitable for treating tissues of the human body. Likewise, treatment of inner ear tissues and/or fluids may involve altering the pressure, volumetric, and temperature characteristics thereof. Imbalances in the pressure levels of such fluids can cause various problems, including but not limited to conditions known as endolymphatic hydrops, endolymphatic hypertension, perilymphatic hypertension, and perilymphatic hydrops.

Due to the risks that certain drugs impose, researchers have developed systems for administering such drugs to aid in the treatment of these ailments and diseases. The systems, devices and methods available are intended to provide sustained release of drugs for obtaining desired physiological or pharmacological effects. However, there are disadvantages associated with their use, including the fact that it is often difficult to obtain the desired release rate and the desired concentration of the drug. This difficulty is largely due to the variability of drug release from the devices, combined with the poorly predictable rate of diffusion of the drug into the inner ear and a dependence upon the precise placement of the device.

While many attempts have been made for treatment of otic ailments, diseases, and disorders, a sustained-release drug device adapted for intracochlear placement, and methods of using said sustained-release drug device have not heretofore been described.

Various embodiments of present invention employs an implanted sustained-release drug device, or pharmaceutical preparations, as described herein, which overcomes these disadvantages. In one embodiment of the invention, the device includes an inner core or reservoir including the effective medicament. Such a device is effective in delivering an effective and sustained concentration of a medicament to the cochlea, thereby obtaining a desired local physiological or pharmacological effect without the complications of systemic administration.

In various embodiments, the sustained-release drug device does not comprise an electrode. In various embodiments, the sustained-release drug device does not have an extra-cochlear portion.

Pharmaceutical Preparations

Various embodiments of the present invention provide for pharmaceutical preparations for sustained-release of an active pharmaceutical ingredient ("API") after cochlear administration or implantation.

In various embodiments, the pharmaceutical preparation for sustained-release of an active pharmaceutical ingredient (API) after cochlear administration or implantation, comprising: 1 to 15 core particles adapted for administration or implantation into the cochlea, wherein each core particle comprises the API, wherein the pharmaceutical preparation is not in a liquid suspension.

In certain embodiments, the pharmaceutical preparation consists essentially of the 1-15 core particles. In certain embodiments, the pharmaceutical preparation consists of the 1-15 core particles.

In certain embodiments, each core particle consists essentially of the API. In certain embodiments, each core particle consists of the API.

In certain embodiments each core particle is one solid API crystal. In certain embodiments, each core particle comprises two or more API crystals, and the two or more API crystals are densely packed together. This can be done using compaction pressures of 0.05-300 GPa, preferably 0.5-5 GPa.

In various embodiments, the API forms a saturated solution within the cochlear fluid after the administering or implanting into the cochlea, and wherein a sustained-release period of the API is determined by the solubility of the API in the cochlear fluid, the turnover of the API from the cochlear fluid, and the amount of the API administered.

In various embodiments, the 1 to 15 core particles are each coated with a first polymeric coating formed from a first polymer-forming solution to form 1 to 15 coated core particles.

In various embodiments, the API forms a saturated solution within the first polymeric coating after the administering or implanting, and wherein the first polymeric coating is permeable to the API during a sustained-release period from administering the API until the concentration of the API contained within the first polymeric coating is unsaturated.

In various embodiments, the pharmaceutical preparation comprises 1, 2, 3, 4, 5, 6, 7, 8, 9, 10, 11, 12, 13, 14 or 15 core particles or coated core particles. In certain embodiments, the pharmaceutical preparation comprises 1-5, 1-10, 5-10, 5-15, or 10-15 core particles or coated core particles. In certain embodiments, the pharmaceutical preparation comprises 1-2, 2-3, 3-4, 4-5, 5-6, 6-7, 7-8, 8-9, or 9-10 core particles or coated core particles. In various embodiments, the pharmaceutical preparation consists essentially of 1, 2, 3, 4, 5, 6, 7, 8, 9, 10, 11, 12, 13, 14 or 15, 1-5, 1-10, 5-10, 5-15, 10-15, 1-2, 2-3, 3-4, 4-5, 5-6, 6-7, 7-8, 8-9, or 9-10 core particles. In various embodiments, the pharmaceutical preparation consists of 1, 2, 3, 4, 5, 6, 7, 8, 9, 10, 11, 12, 13, 14 or 15, 1-5, 1-10, 5-10, 5-15, 10-15, 1-2, 2-3, 3-4, 4-5, 5-6, 6-7, 7-8, 8-9, or 9-10 core particles.

In certain embodiments, the core particle has a maximum dimension of between 100 µm to 300 µm. In certain embodiments, the core particle has a maximum dimension of between 150 µm to 250 µm. In certain embodiments, the core particle has a maximum dimension of between 200 µm to 250 µm.

In various embodiments, the core particle has a high volume to surface area ratio. Examples of high volume to surface area ratios range from 16.7:1 (e.g., for a 100 µm×100 µm cylindrical particle) to 33.3:1 (e.g., for a 200 µm×200 µm cylindrical particle) to 50:1 (e.g., for a 300 µm×300 µm cylindrical particle). The ratio is dependent on the dimensions and shape of the particle. A higher volume:surface area ratio leads to a prolonged release duration per unit of drug.

In various embodiments, diffusion of the API across the first polymeric coating exhibits pseudo-zero-order kinetics during said sustained-release period.

In certain embodiments, the first polymeric coating is substantially degraded after said sustained-release period. In certain embodiments, the first polymeric coating maintains structural integrity during said sustained-release period.

In various embodiments the 1 to 15 core particles or coated core particles are administrable to the perilymph via cochlear implantation or injection.

In certain embodiments, each coated core particle has a maximum diameter between 20 μm and 800 μm and a maximum length of 4 mm. In certain embodiments, each coated core particle has a maximum diameter between 20 μm and 800 μm and a maximum length of 2 mm. In certain embodiments, each coated core particle has a maximum diameter between 20 μm and 800 μm and a maximum length of 1 mm.

In various embodiments, each coated core particle has a maximum dimension between 20 μm and 800 μm, 40 μm and 400 μm, or 100 μm and 250 μm.

In various embodiments, the API is substantially insoluble in the first polymer-forming solution. In certain embodiments, the API is hydrophobic and the first polymer-forming solution is hydrophilic. In certain embodiments, the API is hydrophilic and the first polymer-forming solution is hydrophobic.

In various embodiments, the API is hydrophobic or hydrophilic and the first polymer coats the API via vapor deposition.

In various embodiments, each coated particle further comprises: a second polymeric coating on said first polymeric coating, wherein the second polymeric coating is formed from a second polymer-forming solution, wherein said second polymeric coating is permeable to the API during said sustained-release period.

In various embodiments, each coated particle further comprises: a porous second polymeric coating on the first polymeric coating, wherein the porous second polymeric coating is formed from a second polymer-forming solution, wherein the porous second polymeric coating defines pore regions which permit fluid communication between a pore portion of the first polymeric coating and an external environment, thereby allowing diffusion of the API across the first polymeric coating in the pore regions, and wherein the porous second polymeric coating defines non-pore regions which prevent fluid communication between a non-pore portion of the first polymeric coating and an external environment, thereby inhibiting diffusion of the API across the first polymeric coating in the non-pore regions.

In certain embodiments, second polymeric coating is substantially impermeable to said active pharmaceutical ingredient in the non-pore regions. In certain embodiments, the second polymer-forming solution comprises pore-forming agents which dissolve to produce said pore regions after formation of the second polymeric coating.

In various embodiments, the first polymeric coating comprises a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, para-xylene (parylene N), halogenated para-xylene (i.e. parylene C, parylene HT), β-phenol lactic acid and polyvinyl alcohol.

In various embodiments, the second polymeric coating comprises a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, para-xylene (parylene N), halogenated para-xylene (i.e. parylene C, parylene HT), β-phenol lactic acid and polyvinyl alcohol.

In certain embodiments, the first polymeric coating is applied to said core particle by an air suspension technique. In certain embodiments, the first polymeric coating is applied to said core particle by a dip coating technique. In certain embodiments, the first polymeric coating is applied to said core particle by a vapor deposition technique.

In certain embodiments, the weight of said first polymeric coating is between 0.1% and 200%, 2% and 60%, 0.001% and 20%, 0.001% and 15%, 0.001% and 12%, 0.001% and 10%, 0.001% and 9%, 0.001% and 8%, 0.001% and 7%, 0.001% and 6%, 0.001% and 5%, 0.001% and 4%, 0.001% and 3%, 0.001% and 2%, 0.001% and 1%, 0.001% and 0.1%, or 0.001% and 0.01%, of the weight of said core particle.

In certain embodiments, the volume of said first polymeric coating is between 0.1% and 200%, 2% and 60%, 0.001% and 20%, 0.001% and 15%, 0.001% and 12%, 0.001% and 10%, 0.001% and 9%, 0.001% and 8%, 0.001% and 7%, 0.001% and 6%, 0.001% and 5%, 0.001% and 4%, 0.001% and 3%, 0.001% and 2%, 0.001% and 1%, 0.001% and 0.1%, or 0.001% and 0.01% of the volume of said core particle.

In various embodiments, the API is selected from the group consisting of: an agent for the protection against ototoxicity, an agent for the prevention of sensorineural hearing loss, an agent for the treatment of sensorineural hearing loss, an agent for the protection against inflammation, an agent for the treatment of autoimmune inner ear disease, an agent for the treatment of Meniere's disease, an agent for the prevention of noise induced hearing loss, an agent for the treatment of noise induced hearing loss, an agent for the treatment of infection, and an agent for the treatment of inner ear vestibular dis-function.

In certain embodiments, the API is selected from the group consisting of a growth factor, an antioxidant, a TNF-α inhibitor, a corticosteroid, an antibiotic, an anti-inflammatory drug, and a non-steroidal anti-inflammatory drug.

In certain embodiments, the API is selected from the group consisting of IGF-1, FGF-2, BDNF, reduced glutathione, N-methyl-(D)-glucaminedithiocarbamate and (D)-methionine, infliximab, etanercept, adalimumab, dexamethasone, dexamethasone phosphate, dexamethasone acetate, hydrocortisone, fluticasone proprionate, flusinolone, beclomethasone, triamcinalone, prednisone, prednisolone, methylprednisolone, triamcinolone, ciprofloxacin, finafloxacin, gatifloxacin, levofloxacin, moxifloxacin, ofloxacin, gentamicin, tobramycin, clindamycin, amoxicillin, aspirin, ibuprofen, and naproxen.

In certain embodiments, the API is fluticasone proprionate. In certain embodiments, the API is dexamethasone. In certain embodiments, the API is IGF-1. In certain embodiments, the API is FGF-2. In certain embodiments, the API is BDNF. In certain embodiments, the API is ciprofloxacin.

In various embodiments, the API is a medicine used to treat inner ear tissues. Examples of medicines which are typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), and other drugs, biological materials, and pharmaceutical compositions suitable for treating tissues of the human body.

Another aspect of the invention is a pharmaceutical dosage form comprising a sustained-release device adapted to deliver to the cochlea a therapeutically effective amount of an otoprotective compound, or a pharmaceutically acceptable salt, tautomer solvate, clathrate, prodrug or metabolic derivative thereof.

Sustained-Release Drug Delivery System

Various embodiments of the present invention provide for a sustained-release drug delivery system for delivering a medicament to the cochlea.

In various embodiments, the sustained-release drug delivery system comprises: 1 to 15 devices adapted for administration or implantation into the cochlea, each device comprising: a solid drug core particle comprising the medicament, the solid drug core particle having a maximum diameter between 20 µm and 800 µm and a maximum length of 4 mm, wherein the device is capable of releasing said medicament at a rate which maintains a pharmacologically effective concentration of said medicament within the cochlea, and wherein the 1 to 15 devices are not in a liquid suspension.

In various embodiments, the system further comprises a medical device, wherein the 1 to 15 devices adapted for administration or implantation into the cochlea is attached to the medical device. The medical device; for example, a cochlear implant or other surgically implanted device, can be implanted into, near, or around the cochlea. The medical device can be surgically implanted into the cochlea and explanted as needed.

In certain embodiments, each coated core particle has a maximum diameter between 20 µm and 800 µm and a maximum length of 1 mm.

In certain embodiments, the solid drug core particle consists essentially of the medicament. In certain embodiments, the solid drug core particle consists of the medicament.

In certain embodiments, the solid drug core is one solid medicament crystal. In certain embodiments, the solid drug core comprises two or more medicament crystals, and the two or more medicament crystals are densely packed together. This can be done using compaction pressures of 0.05-300 GPa, preferably 0.5-5 GPa.

In various embodiments, the system comprises 1-5, 1-10, 5-10, 5-15, or 10-15 devices adapted for administration or implantation into the cochlea. In various embodiments, the system comprises 1, 2, 3, 4, 5, 6, 7, 8, 9, or 10 devices adapted for administration or implantation into the cochlea. In various embodiments, the system comprises, 1-2, 2-3, 3-4, 4-5, 5-6, 6-7, 7-8, 8-9 or 9-10 devices adapted for administration or implantation into the cochlea.

In certain embodiments, the core particle has a maximum dimension of between 100 µm to 300 µm. In certain embodiments, the core particle has a dimension diameter of between 150 µm to 250 µm. In certain embodiments, the core particle has a maximum dimension of between 200 µm to 250 µm.

In various embodiments, the core particle has a high volume to surface area ratio. Examples of high volume to surface area ratios range from 16.7:1 (e.g., for a 100 µm×100 µm cylindrical particle) to 33.3:1 (e.g., for a 200 µm×200 µm cylindrical particle) to 50:1 (e.g., for a 300 µm×300 µm cylindrical particle). The ratio is dependent on the dimensions and shape of the particle. A higher volume:surface area ratio leads to a prolonged release duration per unit of drug.

In certain embodiments, the device is capable of maintaining a pharmacologically effective concentration of said medicament within the inner ear for a period of at least 4, 7, 14, 30, 45, 60, 90, 180, days, or at least one year.

In various embodiments, the medicament is selected from the group consisting of: an agent for the protection against ototoxicity, an agent for the prevention of sensorineural hearing loss, an agent for the treatment of sensorineural hearing loss, an agent for the protection against inflammation, an agent for the treatment of autoimmune inner ear disease, an agent for the treatment of Meniere's disease, an agent for the prevention of noise induced hearing loss, an agent for the treatment of noise induced hearing loss, an agent for the treatment of infection, and an agent for the treatment of inner ear vestibular dis-function.

In various embodiments, the medicament is selected from the group consisting of a growth factor, an antioxidant, a TNF-α inhibitor, a corticosteroid, an antibiotic, an anti-inflammatory drug, and a non-steroidal anti-inflammatory drug.

In various embodiments, the medicament is selected from the group consisting of IGF-1, FGF-2, BDNF, reduced glutathione, N-methyl-(D)-glucaminedithiocarbamate and (D)-methionine, infliximab, etanercept, adalimumab, dexamethasone, dexamethasone phosphate, dexamethasone acetate, hydrocortisone, fluticasone proprionate, flusinolone, beclomethasone, triamcinalone, prednisone, prednisolone, methylprednisolone, triamcinolone, ciprofloxacin, finafloxacin, gatifloxacin, levofloxacin, moxifloxacin, ofloxacin, gentamicin, tobramycin, clindamycin, amoxicillin, aspirin, ibuprofen, and naproxen.

In various embodiments, the medicament is fluticasone proprionate. In various embodiments, the medicament is dexamethasone. In certain embodiments, the medicament is IGF-1. In certain embodiments, the medicament is FGF-2. In certain embodiments, the medicament is BDNF. In certain embodiments, the medicament is ciprofloxacin.

Sustained-Release Device

In various embodiments, the device includes an inner core or reservoir including the effective medicament in a polymer-drug matrix form, which in particular can be surrounded by one or more layers of polymer, at least one of which is permeable to the drug. The polymer layers may be applied to the core, or the core may be formed within a pre-manufactured sheath. The size of the device is 1 µm to 4 mm, particularly, about 20 to 800 µm in diameter. This device provides a zero order release profile in vitro over a prolonged time period. Drug-polymer matrices suitable for use in the core of the device can be ones known in the art; for example, as disclosed in international patent application publication no. WO 02/087586, herein incorporated by reference as though fully set forth. Devices of this configuration are known in the art, as disclosed for example in US patent application Pub. No.: US 2007/0003619 A1 and U.S. Pat. No. 6,375,972, herein incorporated by reference and though fully set forth.

Another aspect of the present invention is a method for effectively and safely delivering an effective amount of therapeutic agents, including co-drugs. Co-drugs are described in U.S. Pat. No. 6,051,576 to Ashton et al., the entirety of which is incorporated by reference herein.

One embodiment of the present invention is single drug or co-drug of one or more pharmacologically active compounds in the following classes of agents: anti-inflammatory and analgesic agents, including but not limited to fentanyl citrate and aspirin; non-steroidal anti-inflammatory (NSAID) agents, including but not limited to salicylates, ibuprofen, naproxen; tranquilizing agents, including but not limited to droperidol and prochlorperazine; corticosteroids, including but not limited to dexamethasone, dexamethasone phosphate, dexamethasone acetate, hydrocortisone, fluticasone proprionate, flusinolone, beclomethasone, triamcinalone, prednisone, prednisolone, methylprednisolone, triamcinolone; growth factors (including but not limited to IGF-1, FGF-2, BDNF); antioxidants (including but not limited to reduced glutathione, N-methyl-(D)-glucaminedithiocarbamate and (D)-methionine); TNF-α inhibitors (including but not limited to infliximab, etanercept, adalimumab); volume expanding agents; vasodilating agents, including but not limited to batahistine, niacin and papaverine; antihistaminic agents, including but not limited to meclizine, dimenhydrinate, scopolamene, and promethazine; anticholinergic agents, including but not limited to glycopyrrolate, propantheline, and atropine; antibiotic agents, including but not limited to ampicillin, cefuroxime, ceftriaxone, ciprofloxacin, finafloxacin, gatifloxacin, levofloxacin, moxifloxacin, ofloxacin, gentamicin, tobramycin, clindamycin, amoxicillin; antiviral agents; immunosuppresive agents, including but not limited to cyclophosphomide and cyclosporine; diuretic agents, including but not limited to thiazide, triamterene and carbonic anhydrase inhibitors; antacids and H2-blockers, including but not limited to nizatidine and cimetidine; antiemetics, including but not limited to metoclopramide or diphenidol; calcium channel blockers, including but not limited to diltiazem, nifedipine and verapamil; anticancer agents and drugs; vitamins; vascular rheologic agents; neuroprotective agents; neuromodulators; and anti-apoptotic agents.

Co-drugs in the present invention may include one or more drugs combined as described in U.S. Pat. No. 6,051,576, and below. Co-drugs in the present invention also includes co-drug of a single compound (i.e., a co-drug in which the two active components are the same agent). Those of skill in the art will readily appreciate that the present invention is not limited to the specific agents listed herein, but extends to compounds with desirable therapeutic effects and/or for which the use is indicated for the particular disease state of interest. More detailed lists of the therapeutic agents to which the present invention can be found in, e.g., Goodman & Gilman's The Pharmacologic Basis of Therapeutics (10th ed., McGraw-Hill Companies, Inc., 2001), Remington's Pharmaceutical Sciences (18th ed., Mack Publishing Co., 1990), The Merck Index (12th ed., Merck Research Laboratories, 1996), and other such volumes.

Also included are compositions and devices which gradually erode under the influence of bodily fluids and/or enzymes, and which release a medicament in the process. Such devices and compositions may contain the active medicament itself, or they may contain a relatively insoluble pro-drug which is gradually transformed via chemical or enzymatic action into the active medicament. The drug or pro-drug may be incorporated into an erodible polymer matrix. Also included are solid forms of relatively insoluble medicaments, which simply dissolve slowly over time. These various erodible and pro-drug compositions may be encapsulated or coated, as described above, in order to achieve the desired rate of release with a desired consistency. Numerous devices and compositions have been developed for insertion into other parts of the body, and it is anticipated that most of those that are capable of being manufactured at appropriately small dimensions (20 to 800 μm in diameter) may be adapted for insertion into the cochlea.

Methods of Treatment and Otoprotection

Various embodiments of the present invention provide for a method of administering or implanting into the cochlea, a pharmaceutical preparation to provide sustained-release administration of an API.

In various embodiments, the method comprises providing a pharmaceutical preparation for sustained-release of an API after cochlear administration or implantation; and administering or implanting into the cochlea the pharmaceutical preparation to provide sustained-release administration of the API.

The pharmaceutical preparation can be any pharmaceutical preparation as described herein; for example, those described in the pharmaceutical preparation section above.

In various embodiments, administering or implanting the pharmaceutical preparation is via injecting the pharmaceutical preparation through the round window or the oval window for delivery of API into the cochlea.

In various embodiments, the pharmaceutical preparation is administered during a stapedectomy procedure.

In various embodiments, the pharmaceutical preparation is administered to the perilymph via cochlear implantation or injection.

In various embodiments, the pharmaceutical preparation is attached to a medical device, such as a cochlear implant or other surgically implanted device, and the medical device is implanted into, near or around the cochlea.

In various embodiments, the pharmaceutical preparation is attached to a medical device which can be surgically implanted into the cochlea and explanted as needed.

In various embodiments, the surgical procedure to administer or implant into the cochlea is via the middle ear or mastoid. In various embodiments, the procedure for insertion of the particle via the middle ear or mastoid into the cochlea can be substantially the same as those described in the examples herein. When the particle alone is placed into the cochlea, it is sealed in, as the cochlea is a sequestered from the rest of the ear.

In various embodiments, administering or implanting into the cochlea the pharmaceutical preparation to provide sustained-release administration of the API protects against ototoxicity, reduces the risk of sensorineural hearing loss, treats of sensorineural hearing loss, protects against inflammation, treats autoimmune inner ear disease, treats Meniere's disease, reduces the risk of noise induced hearing loss, treats of noise induced hearing loss, treats infection, or treats inner ear vestibular dis-function. One of ordinary skill in the art will readily appreciate how to select the appropriate API/medicament to use for each of these disease conditions or disorders. The appropriate API/medicament can be prepared into the pharmaceutical preparation as discussed herein or as known by one of ordinary skill in the art.

In various embodiments administering or implanting into the cochlea the pharmaceutical preparation to provide sustained-release administration of the API treats or reduces the risk of sensorineural hearing loss, chemically-induced hearing loss, noise-induced hearing loss, inflammation, autoimmune inner ear diseases, Menier's disease, or otitis media. Examples of these diseases and disorders are discussed herein; for example, in the background of the invention.

Otoprotective agents are useful in the context of coping with the hazards to hearing posed by loud noises in certain occupational or recreational activities, or injuries arising from aging, inflammation, disease, or exposure to ototoxic chemicals, if they could be delivered consistently to the inner ear at effective concentrations. The invention provides methods for using such otoprotective agents, which are useful for counteracting the ototoxic side-effects associated with certain chemotherapeutic regimes, and for improving quality of life in aging populations experiencing progressive hearing impairment.

One aspect of the invention is a method for preventing, reducing or treating ototoxicity in a subject undergoing treatment with an ototoxic chemotherapeutic drug, such as one selected from an aminoglycoside antibiotic, a macrolide antibiotic, a glycopeptide antibiotic, a platinum-containing antineoplastic agent, certain quinine-like compounds or an ototoxic loop diuretic drug, by implanting into the ear of a subject in need of such treatment a sustained-release drug delivery device capable of delivering a therapeutic dosage of an otoprotective agent, a pharmaceutical preparation, or sustained-release drug delivery system as disclosed herein. Representative aminoglycoside antibiotics include, but are not limited to, amikacin (BB-K8), butirosin, geneticin, gentamicin, kanamycin, lividomycin, neomycin, paromomycin, hybrimycin, propikacin (UK 31214), ribostamycin, seldomycin, trehalosamine, $\alpha$-D-mannosyl-$\alpha$-D-glucosaminide, apramycin, bluensomycin, netromycin, streptomycin, tobramycin, sisomicin, destomycin, Antibiotic A-396-I, dibekacin, kasugamycin, fortimicin, or derivatives, analogs or variants thereof. Representative macrolide antibiotics include, but are not limited to, erythromycin and azithromycin, and a representative glycopeptide antibiotic is vancomycin.

Methods of implanting electrodes and other intra-cochlear devices are known in the art, as are methods of introducing solutions via cannulas and needles. One of ordinary skill in the art will readily appreciate that these methods can be adapted for implantation of the sustained-delivery devices of the present invention.

Another aspect of the present invention relates to methods for augmenting treatments which require administration of an ototoxic chemical or chemotherapeutic agent comprising of administering an effective amount of an otoprotective agent to prevent, reduce or treat the hearing impairment caused by the ototoxic agent. In certain embodiments, the otoprotective agent and chemotherapeutic agent may be provided as a kit in which each is provided in appropriate dosage forms, along with instructions for co-administering the two agents.

In one embodiment, the device may be implanted prior to, simultaneously with, or subsequent to administration of said ototoxic chemotherapeutic agent.

In a certain embodiment, the invention provides a method wherein a therapeutically effective amount of otoprotective composition is administered to prevent, reduce, or otherwise treat hearing impairment due to NIHL, wherein the otoprotective agent is administered between 72 hours before, and 36 hours after exposure to otodestructive noise. The particular timing of administration will be dependent on the times during which the otoprotective agent exhibits the desired otoprotective effects.

In a certain embodiment, the invention provides a method wherein a therapeutically effective amount of otoprotective composition, a pharmaceutical preparation as described herein, or sustained-release drug delivery system as described herein is administered to prevent, reduce, or otherwise treat hearing impairment due to autoimmune inner ear disease.

In a certain embodiment, the invention provides a method wherein a therapeutically effective amount of otoprotective composition, a pharmaceutical preparation as described herein, or sustained-release drug delivery system as described herein is administered to prevent, reduce, or otherwise treat hearing impairment due to Meniere's disease.

In a certain embodiment, the invention provides a method wherein a therapeutically effective amount of medicament composition, a pharmaceutical preparation as described herein, or sustained-release drug delivery system as described herein is administered to prevent, reduce, or otherwise treat inner ear damage due to inflammation.

In a certain embodiment, the invention provides a method wherein a therapeutically effective amount of medicament composition, a pharmaceutical preparation as described herein, or sustained-release drug delivery system as described herein is administered to prevent, reduce, or otherwise treat infections of the inner ear.

In other embodiments, the invention provides methods and compositions for delivering therapeutic drugs to the cochlea, such as antibiotics, neurologically active agents, growth factors, and the like.

The present invention also relates to methods useful for treating a patient for disorders of the ear or its adjacent structures, and more particularly treating otic disorders in mammals.

In various embodiments, the present invention provides a method for the placement, controlled and sustained release of a composition effective in obtaining a desired local or systemic physiological or pharmacological effect, a pharmaceutical preparation as described herein, or a sustained-release drug delivery system as described herein.

In one embodiment the invention constitutes a method for treating a mammal having or prone to a hearing (or balance) impairment or treating a mammal prophylactically to prevent or reduce the occurrence or severity of a hearing (or balance) impairment that would result from inner ear cell injury, loss, or degeneration.

The method includes positioning a sustained released drug delivery system as described herein, or a pharmaceutical preparation as described herein, at an area wherein release of the agent is desired and allowing the agent to pass through the device to the desired area of treatment.

Various embodiments of the invention provide a method for direct implantation of a drug delivery device, a pharmaceutical preparation as described herein, or a sustained-release drug delivery system as described herein in to the cochlea. Such devices provide sustained controlled release of various compositions to treat the inner ear without risk of detrimental local and systemic side effects. In particular embodiments, such devices use a diffusion mechanism in delivery of the agents to the treatment area. In particular embodiments, the device maintains an effective concentration of the drug for at least 4 days, particularly, 7 days, 30 days, 180 days, and at least one year.

Accordingly an aspect of the invention is a method of treating a condition of the ear of a mammal comprising accessing the cochlea and placing or implanting a drug delivery device, a pharmaceutical preparation as described herein, or a sustained-release drug delivery system as described herein in the cochlea.

The present inventors have discovered a method that is suitable for the placement, controlled and sustained release of an agent or drug effective in obtaining a desired local physiological or pharmacological effect.

The present invention includes implanting drug delivery devices to deliver therapeutic agents, as described in this application, to a localized anatomical site within the inner ear. Drug delivery devices that are usable or adapted to be usable in the present invention can be, for example, as described by US Patent Application Pub. No.: US 2007/0003619, the entirety of which is incorporated by reference. When a method in accordance with the present invention necessitates the use of more than one such device, either for delivery of more than one medicament or in order to deliver sufficient medicament, another aspect of the present invention is using two or more drug delivery devices, which may be the same or different. It will be appreciated that the devices described, in order to be useful in the present invention, must be adapted for insertion into the cochlea as described elsewhere in this disclosure.

A particular embodiment of the present invention is a method for safely delivering an effective amount of a therapeutic agent, or a pro-drug or co-drug, by inserting into the cochlea an implantable drug delivery device. In particular embodiments, the device functions by a diffusion mechanism.

In particular embodiments, the present invention provides for a method for delivering an effective amount of therapeutic agents, including co-drugs and pro-drugs, using implantable drug delivery devices as described in US Patent Application Pub. No.: US 2007/0003619.

Yet another particular embodiment of the present invention is a method for delivering, for an extended period of time, an effective amount of therapeutic agents to an affected site. Long term delivery of therapeutic agents is one particular embodiment of the present invention. Therefore, the present invention includes a drug delivery device that is placed within the cochlea and is capable of delivering a therapeutic agent for at least four days. In particular embodiments, the duration of the drug delivery through the implanted drug delivery device to the effected site is months to years. In certain embodiments, the delivery of these therapeutic agents is linear in nature and the dosage is capable of remaining at therapeutic levels for weeks, months, or years.

There are several aspects to the present invention. In general, one aspect of the present invention is the treatment of conditions associated with the ear by avoiding systemic administration and delivery of active medication, to thereby reduce, minimize, or eliminate the associated side effects. Therefore, an aspect of the present invention is the localized delivery of medication to the cochlea, using a drug delivery device which is implantable.

Specifically, the present invention provides a method for treating inner ear diseases and their associated symptoms including, but not limited to, congenital abnormalities such as congenital syphilis and toxoplasmosis; viral or bacterial infections; cancers; and acquired inner ear diseases such as Meniere's disease, autoimmune inner ear disease, sensory neuronal hearing loss or ototoxicity. Another aspect involves maintaining the integrity or keeping cochlear hair cells intact within the inner ear. A goal is, therefore, to leave vestibular hair cells intact. Thus, it would be advantageous to administer gentamicin to a patient via a local route of administration and thereby avoid undesirable side effects of systemic administration.

More particularly, senility- and noise-induced loss of hearing can be treated according to the present invention. It is known that there is an apoptosis of hair cells within the cochlear ear channels associated with some of these conditions. According to the present invention, this condition may be treated by administering drugs directly to the inner ear in order to minimize or delay this senility- or noise-induced hearing loss. Typical pharmaceutical compounds that may be useful include the calcium channel blocking agents, cyclosporins, as well as steroids.

Devices and methods in accordance with the present invention can also advantageously be used in the treatment of Meniere's disease. Particular medications which may be used in treating this disease are mentioned above and include, but not limited to, vasodilators, diuretics and steroids.

Another aspect of the present invention is the surgical implantation of a drug delivery device. In certain embodiments, the surgical implantation can include larger scale cutting of the tissues of the patient in order to access the anatomical site in which the drug delivery device is to be implanted.

In the methods of preventing or reducing ototoxicity of the present invention, various parameters associated with the patient's hearing and vestibular systems can be tested by methods well known in the art to establish pretreatment baseline values. After administration of the methionine protective agent, and over the course of chemotherapy and afterwards, ototoxic effects can be monitored by conventional tests, and the results can be compared to those obtained prior to treatment to determine if any change has occurred. If any impairment is observed, the amount and/or time of administration of the protective agent administered in conjunction with subsequent doses of the platinum-containing chemotherapeutic agent, loop diuretic agent, aminoglycoside antibiotic, iron chelating agent, quinine, quinidine, or exposure to noise or radiation, can be adjusted so as to reduce or prevent further ototoxic changes without substantially diminishing the antineoplastic effectiveness of the platinum-containing chemotherapeutic agent or radiation, the diuretic effect of the loop diuretic agent, etc. Similar modification of treatment parameters in the case of weight loss, gastrointestinal toxicity due to either the platinum-containing chemotherapeutic agent or radiation, neurotoxicity due to either the platinum-containing chemotherapeutic agent or radiation, alopecia due to either the platinum-containing chemotherapeutic agent or radiation, and overall patient condition/survival due to either the platinum-containing chemotherapeutic agent or radiation can be employed to optimize the protective effects of the protective agent with respect thereto. This can be achieved via appropriate testing and comparison of pre- and post-treatment values, e.g., patient weight and patient physical/medical/physiological condition, etc., with protocol adjustments being made as needed.

Packaged Pharmaceutical Products

Various embodiments of the present invention provide for a packaged pharmaceutical product, comprising: a sustained release drug delivery system as described herein as described herein; and instructions for using the system in conjunction with administration of an ototoxic chemotherapeutic drug. In certain embodiments, the packaged pharmaceutical product further comprises the ototoxic chemotherapeutic drug. Examples of ototoxic chemotherapeutic drugs are described herein.

Various embodiments of the present invention provide for a packaged pharmaceutical product, comprising: a sustained release drug delivery system or pharmaceutical preparation as described herein; and instructions for using the system in conjunction with the implantation of a medical device into the cochlea.

Various embodiments of the present invention provide for a packaged pharmaceutical product, comprising: a pharmaceutical preparation as described herein as described herein; and instructions for using the pharmaceutical preparation in conjunction with administration of an ototoxic chemotherapeutic drug. In certain embodiments, the packaged pharmaceutical product further comprises the ototoxic chemotherapeutic drug. Examples of ototoxic chemotherapeutic drugs are described herein.

Various embodiments of the present invention provide for a packaged pharmaceutical product, comprising: a pharmaceutical preparation for sustained-release of an API after cochlear administration or implantation as described herein; and instructions for using the pharmaceutical preparation to administer or implant the pharmaceutical preparation to the cochlea.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Intracochlear Fluticasone Proprionate Levels Following Implantation, Study A

Sustained Release Coating: Fluticasone propionate crystals were coated with polyvinyl alcohol (PVA).

Figure 3:
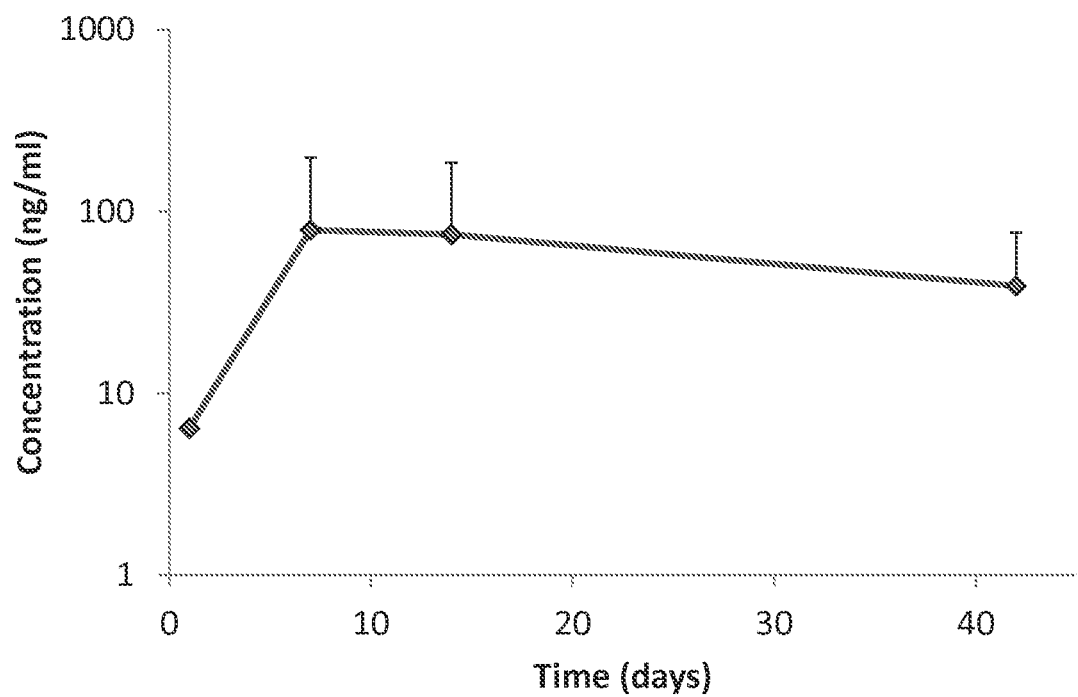
FIG. 3 depicts data regarding in vivo release of an active pharmaceutical ingredient (fluticasone proprionate) from coated particles of the invention over a sustained-release period in the cochlea of an animal model (guinea pig *cochleae*) in accordance with various embodiments of the present invention.

In vivo studies; see FIG. 3:

Surgery: Albino guinea pigs were used for the single dose intracochlear implantation experiment. The guinea pigs received a single implant in one of their ears, and the other ear was used as internal control. Under general anesthesia, a postauricular incision was made over the bulla in the experimental ear. A small hole was drilled through the bulla using a posterior approach. The ear was positioned with the round window facing horizontally and superiorly. A 32-gauge needle was used to puncture the round window and the particle was put in contact with the perilymph in the scala tympani. A blood drop was placed over the round window injection site to avoid leakage of perilymphatic fluids and a suture was used to close the wound.

Pharmacokinetic: Perilymph samples were obtained at 1, 7, 14 and 42 days after implantation and the fluticasone concentration in each sample was measured by HPLC.

Example 2

Intracochlear Fluticasone Proprionate Levels Following Implantation, Study B

Sustained Release Coating: Fluticasone propionate crystals were coated with polyvinyl alcohol (PVA).

Figure 4A:
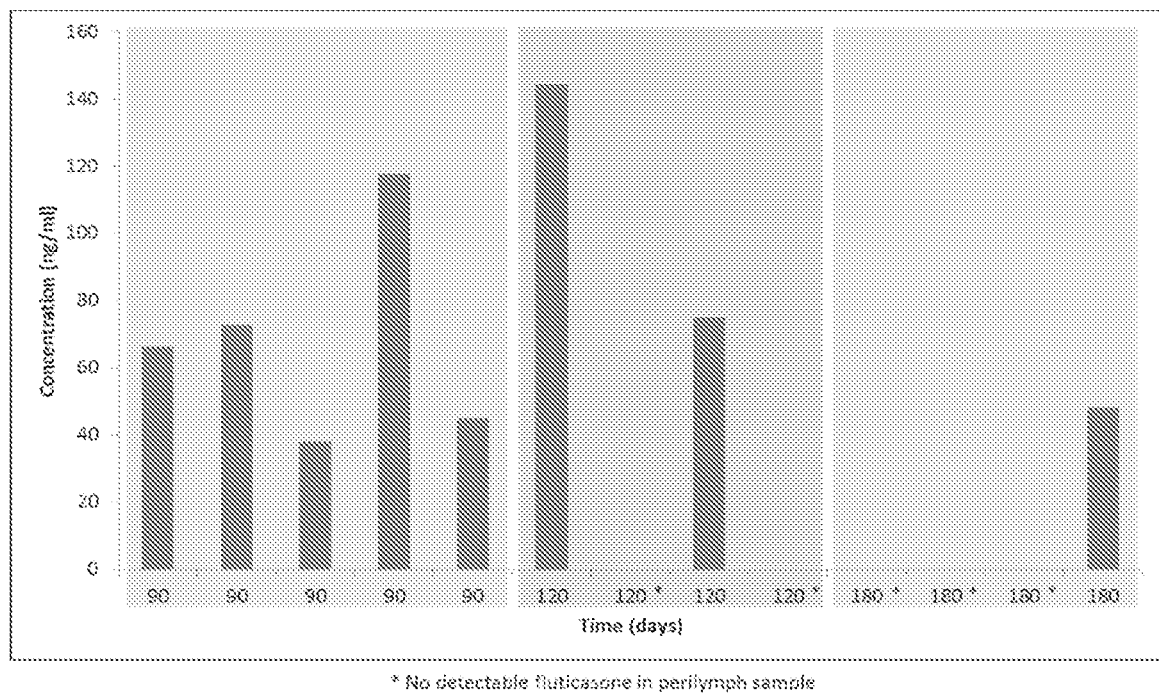
FIGS. 4A and 4B depict intracochlear fluticasone proprionate concentration following implantation in accordance with various embodiments of the present invention.
Figure 4B:
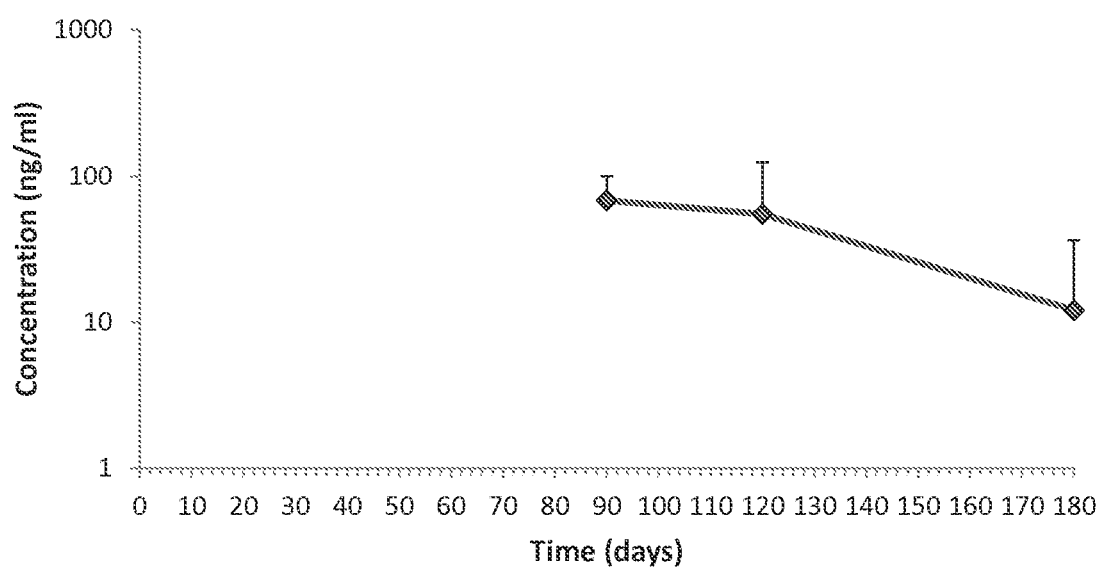

In vivo studies; see FIGS. 4A and 4B:

Surgery: Albino guinea pigs were used for the single dose intracochlear implantation experiment. The guinea pigs received a single implant in one of their ears, and the other ear was used as internal control. Under general anesthesia, a postauricular incision was made over the bulla in the experimental ear. A small hole was drilled through the bulla using a posterior approach. The ear was positioned with the round window facing horizontally and superiorly. A 32-gauge needle was used to puncture the round window and the particle was put in contact with the perilymph in the scala tympani. A blood drop was placed over the round window injection site to avoid leakage of perilymphatic fluids and a suture was used to close the wound.

Pharmacokinetic: Perilymph samples were obtained at 90, 120, and 180 days after implantation and the fluticasone concentration in each sample was measured by HPLC. N=5 (day 90) or N=4 (day 120 and 180).

Example 3

Hearing Tests Following Intracochlear Fluticasone Proprionate Particle Implantation Study Design: The animals from Example 2 underwent hearing tests to ascertain the safety of the extended release fluticasone proprionate implant. Hearing was tested pre-implant (N=15), 90 (N=5), 120 (N=5), and 180 (N=5) days post-implant. Implanted ears were compared to ears that did not undergo surgery.

Figure 5A:
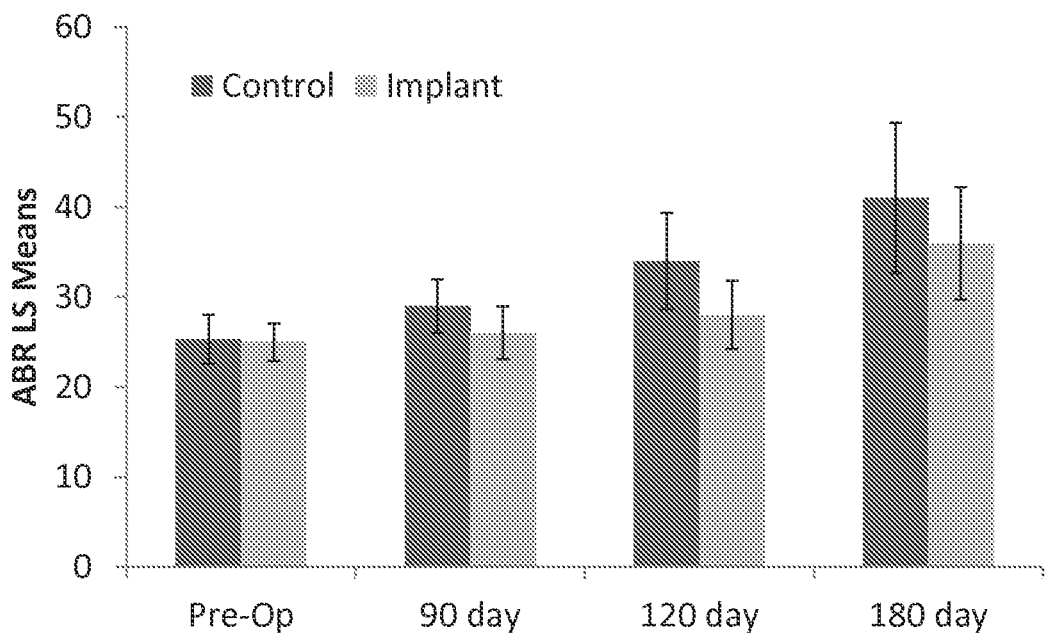
FIGS. 5A and 5B depicts the results of hearing tests following intracochlear fluticasone proprionate particle implantation in accordance with various embodiments of the present invention.
Figure 5B:
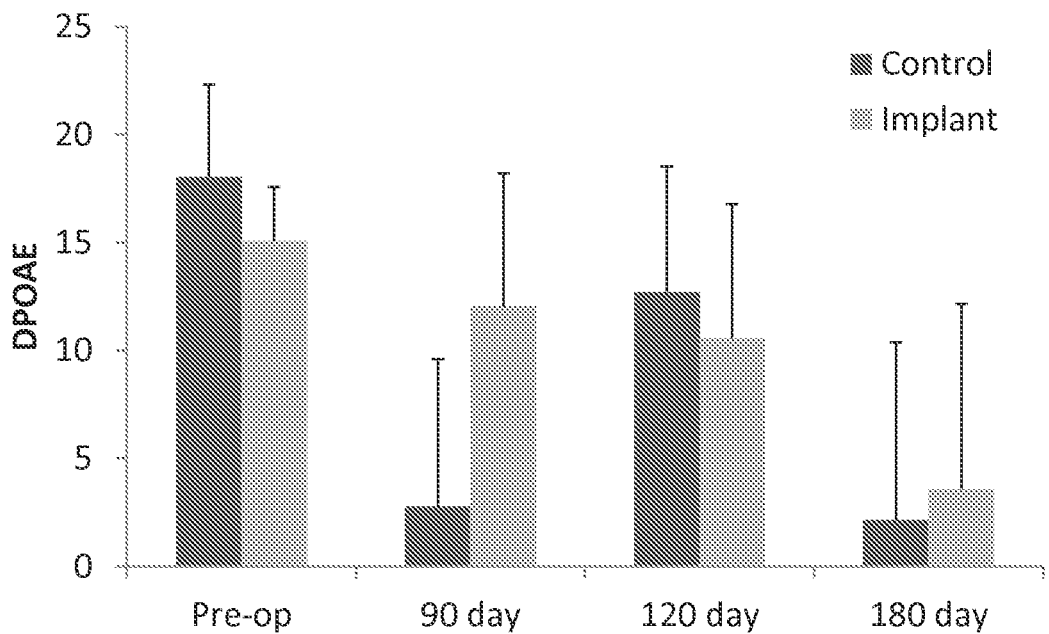

Auditory Measurements; see FIGS. 5A and 5B: Animals were anesthetized for auditory testing. Briefly, ABRs were measured under computer control in response to clicks 50 µs duration from levels below threshold to 80 dB SPL in 5 dB steps. Responses were detected with subcutaneous needle electrodes placed at the vertex and ventrolateral to the left and right pinna. Response was amplified (10,000 times), filtered (0.1-3 kHz bandpass) and averaged (across 512 sweeps at each frequency-level combination). On visual inspection of stacked waveforms, "threshold" was defined as the lowest stimulus level at which response peaks are clearly present. These visual detection threshold judgments were confirmed following termination of the experiment by offline display and analysis of the stored waveforms. Lower ABR LS Means reading indicates better hearing. Error bars indicate Standard Error.

DPOAE (2f1-f2) Input/output functions were recorded. Response amplitude was recorded as a function of L2 (L1-L2=10 dB); primaries incremented together in 5 dB steps (from 20 to 80 dB SPL) spanning the frequency range f2=5.6-45.2 kHz (f2/f1=1.2). Ear-canal sound pressures were amplified, digitally sampled, averaged until a SNR of 6 dB is achieved. DPOAE level at 2f1-f2 and surrounding noise floor values (±50 Hz of 2f-f2) were extracted. Higher DPOAE reading indicates better hearing. Error bars indicate Standard Error.

Example 4

Intracochlear Fluticasone Proprionate for Otoprotection of Cisplatin Dependent Hearing Loss Study Design: Particles were created and implanted into guinea pig *cochleae* as described in Examples 1-2. The study design is as follows:

Each animal: one ear implanted with extended release fluticasone particle ("implant ear"), other ear served as internal control ("control ear").

Hearing was assessed via click (broad frequency) ABRs and DPOAE

Figure 6A:
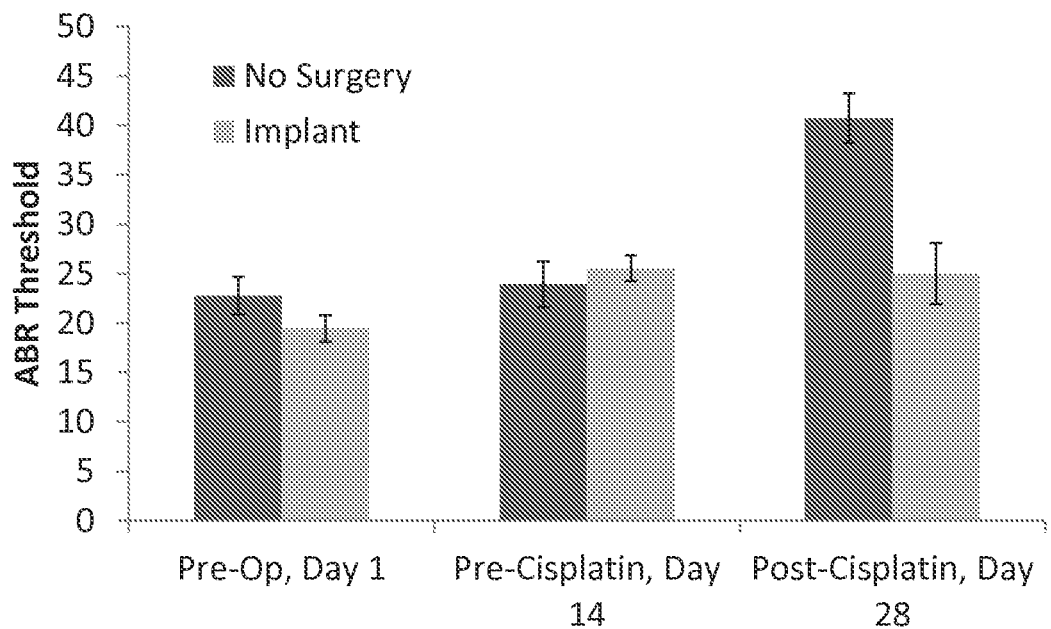
FIGS. 6A and 6B depicts the results of intracochlear fluticasone proprionate for otoprotection of cisplatin dependent hearing loss in accordance with various embodiments of the present invention.
Figure 6B:
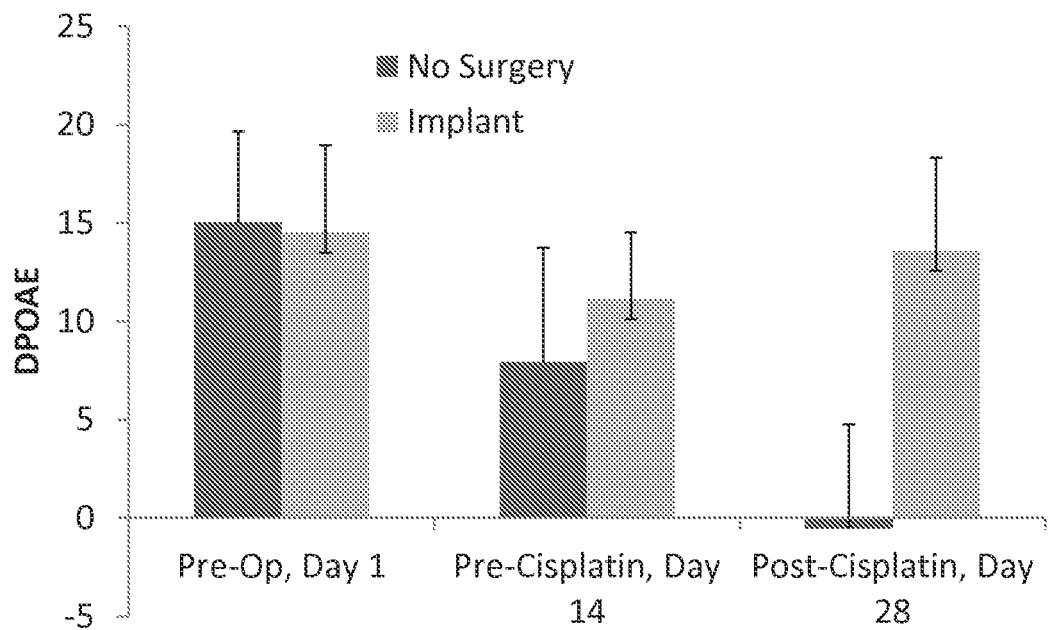

No statistically significant hearing loss was observed between control and surgery ears at day 14, suggesting no effect of implant surgery on the ABR threshold. Statistically significant hearing loss was seen in "control ears" following cisplatin treatment via ABR threshold at day 14 and day 28: 23.9±2.3 dB vs. 40.7±2.5 dB; P≤0.0001, thus demonstrating cisplatin dependent hearing loss. No significant difference in ABR threshold between surgery ears at day 14 and following cisplatin treatment at day 28: 25.6±1.3 dB vs. 25.0±3.1 dB, P≥0.85, demonstration particle dependent prevention of cisplatin-induced hearing loss. DPOAE results indicate that the steroid implant prevents cisplatin-induced damage of the cochlear amplification process. As shown in the FIG. 6B, at 14 days after cisplatin application, DPOAE responses were absent in control ears but near normal in those implanted with particles. Error Bars indicate Standard Error.

Example 5

Intracochlear Dexamethasone for Trauma Protection (Hearing)

Study design: The Eshraghi trauma insertion procedure (Eshraghi, A., et al., *Local dexamethasone therapy conserves hearing in an animal model of electrode insertion trauma-induced hearing loss*. OTOL NEUROTOL, 2007. 28(6): p. 842-9) was adapted for use in these studies. Briefly, a cochleostomy was introduced into animals and a 35 gauge stainless steel dummy electrode was inserted 3 mm into the cochlea. Test conditions were as follows: (1) no treatment, (2) addition of a single 5 μg extended release dexamethasone pellet, (3) addition of a single 10 μg extended release dexamethasone pellet, (4) addition of five 10 μg extended release dexamethasone pellets (50 μg total dose).

The addition of trauma using this technique significantly impaired the hearing of the animals. The addition of sustained release dexamethasone preserved hearing in a dose dependent manner, with 5 μg of dexamethasone improving hearing over no treatment and 10 and 50 μg dexamethasone improving hearing to an even greater extent.

Figure 7:
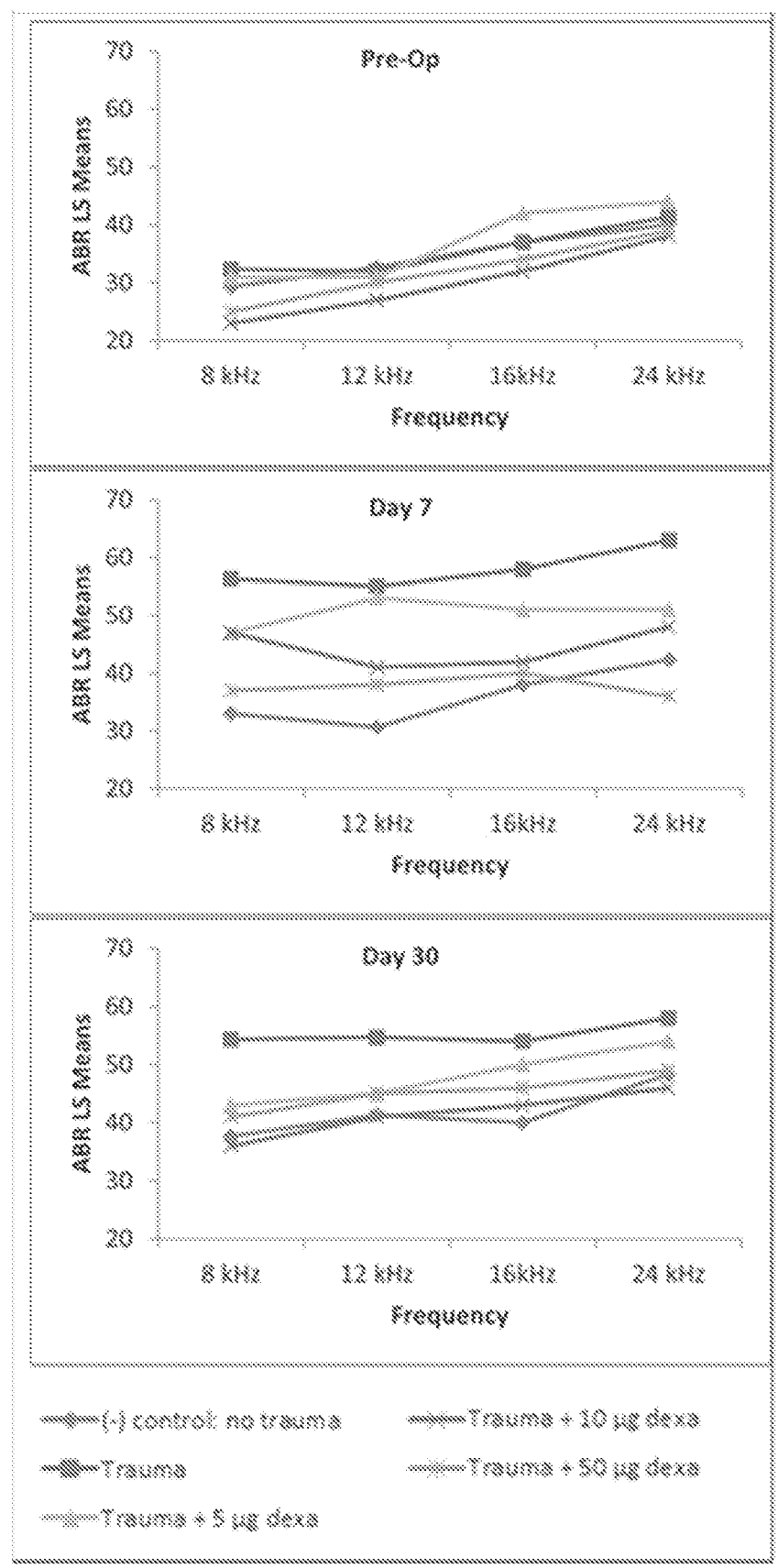
FIG. 7 depicts the results of intracochlear dexamethasone for trauma protection (hearing) in accordance with various embodiments of the present invention.
Figure 8:
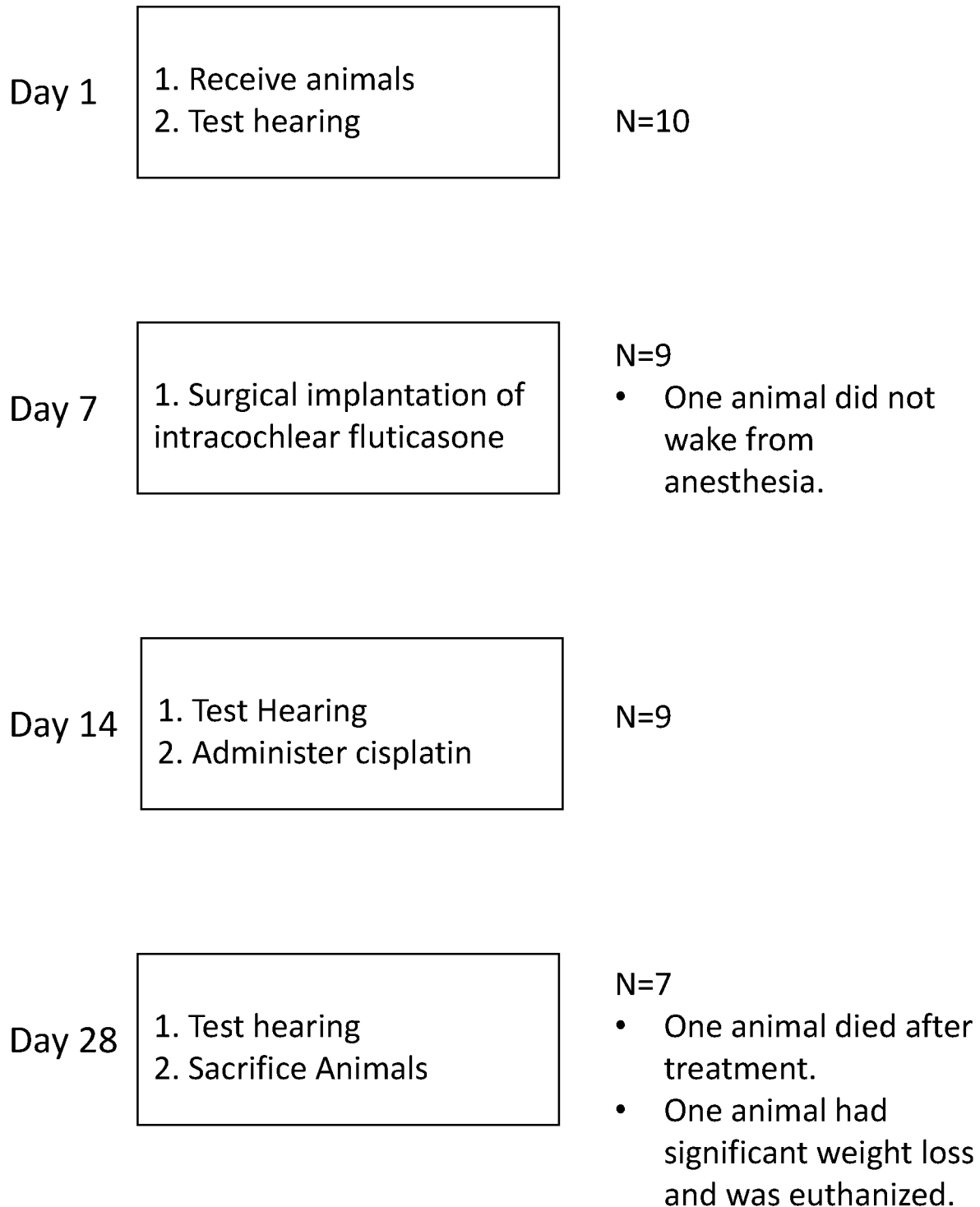
FIG. 8 depicts an exemplary study design showing intracochlear fluticasone proprionate for otoprotection of cisplatin dependent hearing loss in accordance with various embodiments of the present invention.

Auditory Measurements; see FIG. 7: The animals from Example 2 underwent hearing tests to ascertain the safety of the sustained release fluticasone proprionate implant. Hearing was tested pre-implant (N=15), 90 (N=5), 120 (N=5), and 180 (N=5) days post-implant. Implanted ears were compared to ears that did not undergo surgery. Animals were anesthetized for auditory testing. Briefly, ABRs were measured under computer control in response to clicks 50 μs duration from levels below threshold to 80 dB SPL in 5 dB steps. Responses were detected with subcutaneous needle electrodes placed at the vertex and ventrolateral to the left and right pinna. Response was amplified (10,000 times), filtered (0.1-3 kHz bandpass) and averaged (across 512 sweeps at each frequency-level combination). On visual inspection of stacked waveforms, "threshold" was defined as the lowest stimulus level at which response peaks are clearly present. These visual detection threshold judgments were confirmed following termination of the experiment by offline display and analysis of the stored waveforms.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

The invention claimed is:

1. A method of treating a pathological condition of an inner ear, comprising:
   puncturing a round window or an oval window of a subject's ear in need thereof; and
   implanting into a cochlea 1-15 core particles alone or 1-15 coated core particles alone for sustained release of an active pharmaceutical ingredient (API) by placing the 1-15 core particles or the 1-15 coated core particles through the puncture in the round window or through the puncture in the oval window for delivery of the API into the cochlea to provide sustained release administration of the API,
   wherein the core particle is one solid API crystal, or wherein each core particle is two or more API crystals that are densely packed together,
   wherein the 1-15 core particles or 1-15 coated core particles provide sustained-release of the API for at least four days,
   wherein a pharmacologically effective concentration of the API within the cochlea is maintained for at least four days,
   wherein each core particle has a maximum dimension of 300 um,
   wherein the 1-15 core particles or the 1-15 coated core particles are not in a liquid suspension prior to implantation, and wherein after implantation, the 1-15 core particles or the 1-15 coated core particles are not attached to an electrode, and are not attached to a device having an extra-cochlear portion.

2. The method of claim 1, wherein each core particle is one solid API crystal.

3. The method of claim 1, wherein the API forms a saturated solution within the cochlear fluid after the implanting into the cochlea, and wherein a sustained-release period of the API is determined by the solubility of the API in the cochlear fluid, the turnover of the API from the cochlear fluid, and the amount of the API administered.

4. The method of claim 1, wherein the 1-15 core particles are each coated with a first polymeric coating formed from a first polymer-forming solution to form the 1-15 coated core particles.

5. The method of claim 4, wherein the API forms a saturated solution within the first polymeric coating after the implanting, and wherein the first polymeric coating is permeable to the API during a sustained-release period from administering the API until the concentration of the API contained within the first polymeric coating is unsaturated.

6. The method of claim 1, wherein 1-10 core particles or coated core particles are provided and implanted.

7. The method of claim 1, wherein 1-5 core particles or coated core particles are provided and implanted.

8. The method of claim 1, wherein the core particle has a maximum dimension of 100 µm.

9. The method of claim 1, wherein the core particle has a maximum diameter of 150 µm.

10. The method of claim 1, wherein the core particle has a maximum dimension of 200 µm.

11. The method of claim 1, wherein the core particle has a high volume to surface area ratio.

12. The method of claim 4, wherein diffusion of the API across the first polymeric coating exhibits pseudo-zero-order kinetics during said sustained-release period.

13. The method of claim 4, wherein the first polymeric coating is degraded after said sustained-release period.

14. The method of claim 4, wherein the first polymeric coating maintains structural integrity during said sustained-release period.

15. The method of claim 4, wherein each coated core particle has a maximum dimension of 250 µm.

16. The method of claim 4, wherein each coated core particle has a maximum dimension of 40 m.

17. The method of claim 4, wherein each coated core particle has a maximum dimension of 100 µm.

18. The method of claim 4, wherein the API is insoluble in the first polymer-forming solution.

19. The method of claim 4, wherein the API is hydrophobic and the first polymer-forming solution is hydrophilic, or wherein the API is hydrophilic and the first polymer-forming solution is hydrophobic.

20. The method of claim 4, wherein each coated particle further comprises:
a second polymeric coating on said first polymeric coating, wherein the second polymeric coating is formed from a second polymer-forming solution,
wherein said second polymeric coating is permeable to the API during said sustained-release period; or
a porous second polymeric coating on the first polymeric coating, wherein the porous second polymeric coating is formed from a second polymer-forming solution,
wherein the porous second polymeric coating defines pore regions which permit fluid communication between a pore portion of the first polymeric coating and an external environment, thereby allowing diffusion of the API across the first polymeric coating in the pore regions, and
wherein the porous second polymeric coating defines non-pore regions which prevent fluid communication between a non-pore portion of the first polymeric coating and an external environment, thereby inhibiting diffusion of the API across the first polymeric coating in the non-pore regions.

21. The method of claim 4, wherein the first polymeric coating comprises a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, para-xylene, halogenated para-xylene, O-phenol lactic acid and polyvinyl alcohol, and the second polymeric coating comprises a polymer or co-polymer including at least one monomer selected from the group consisting of sugar phosphates, alkylcellulose, hydroxyalkylcelluloses, lactic acid, glycolic acid, β-propiolactone, β-butyrolactone, γ-butyrolactone, pivalolactone, α-hydroxy butyric acid, α-hydroxyethyl butyric acid, α-hydroxy isovaleric acid, α-hydroxy-β-methyl valeric acid, α-hydroxy caproic acid, α-hydroxy isocaproic acid, α-hydroxy heptanic acid, α-hydroxy octanic acid, α-hydroxy decanoic acid, α-hydroxy myristic acid, α-hydroxy stearic acid, α-hydroxy lignoceric acid, para-xylene, halogenated para-xylene, O-phenol lactic acid and polyvinyl alcohol.

22. The method of claim 4, wherein said first polymeric coating is applied to said core particle by an air suspension technique, a dip coating technique, or a vapor deposition technique.

23. The method of claim 4, wherein the weight of said first polymeric coating is between 0.001% and 60% of the weight of said core particle, or the volume of said first polymeric coating is between 0.001% and 60% of the volume of said core particle.

24. The method of claim 1, wherein the 1-15 core particles or 1-15 coated core particles is implanted during a stapedectomy procedure.

25. The method of claim 1, wherein the method protects against ototoxicity, reduces the risk of sensorineural hearing loss, treats of sensorineural hearing loss, protects against inflammation, treats autoimmune inner ear disease, treats Meniere's disease, reduces the risk of noise induced hearing loss, treats of noise induced hearing loss, treats infection, or treats inner ear vestibular dis-function.

26. The method of claim 21, wherein the halogenated paraxylene is parylene C.

27. The method of claim 1, wherein the core particle has a maximum dimension of 250 µm.

28. The method of claim 1, wherein pharmacologically effective concentration of the API within the inner ear is maintained for at least 30 days.

29. The method of claim 1, wherein pharmacologically effective concentration of the API within the inner ear is maintained for at least 180 days.

30. The method of claim 1, wherein the API is selected from the group consisting of IGF-1, FGF-2, BDNF, reduced glutathione, N-methyl-(D)-glucaminedithiocarbamate and (D)-methionine, infliximab, etanercept, adalimumab, dexamethasone, dexamethasone phosphate, dexamethasone acetate, hydrocortisone, fluticasone proprionate, flusinolone, beclomethasone, triamcinalone, prednisone, prednisolone, methylprednisolone, triamcinolone, ciprofloxacin, finafloxacin, gatifloxacin, levofloxacin, moxifloxacin, ofloxacin, gentamicin, tobramycin, clindamycin, amoxicillin, aspirin, ibuprofen, and naproxen.

31. The method of claim 1, wherein the API is fluticasone proprionate.

32. A method of providing otoprotection of cisplatin dependent hearing loss, comprising:
    puncturing a round widow or an oval window of a subject's ear; and
    implanting into the cochlea 1 to 15 coated core particles adapted for sustained-release of an active pharmaceutical ingredient (API) by placing the 1-15 coated core particles alone through the puncture in the round window or through puncture in the oval window for delivery of the API into the cochlea to provide sustained-release administration of the API and thereby provide otoprotection of cisplatin dependent hearing loss,
    wherein each core particle is one solid API crystal, or wherein each core particle is two or more API crystals that are densely packed together,
    wherein the API is fluticasone propionate,
    wherein each core particle, prior to coating, has a maximum dimension of 250 μm, wherein each core particle is coated with a first polymeric coating formed from a first polymer-forming solution to form the 1-15 coated core particles,
    wherein the first polymeric coating is polymers of lactic acid, polymers of glycolic acid, polymers of para-xylene, polymers of halogenated para-xylene, or polymers of polyvinyl alcohol, and
    wherein a pharmacologically effective concentration of the API within the inner ear is maintained for at least 7 days,
    wherein the 1-15 coated core particles are not in a liquid suspension prior to implantation, and
    wherein after implantation, the 1-15 coated core particles are not attached to an electrode, and are not attached to a device having an extra-cochlear portion.

* * * * *